(12) United States Patent
Bourelle et al.

(10) Patent No.: US 11,571,360 B2
(45) Date of Patent: Feb. 7, 2023

(54) HAND-HELD FLUID TRANSFER DEVICE AND SYSTEM

(71) Applicant: ENABLE INJECTIONS, INC., Cincinnati, OH (US)

(72) Inventors: Dylan Bourelle, Cincinnati, OH (US); Matthew J. Huddleston, Loveland, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 404 days.

(21) Appl. No.: 16/621,909

(22) PCT Filed: Jun. 14, 2018

(86) PCT No.: PCT/US2018/037624
§ 371 (c)(1),
(2) Date: Dec. 12, 2019

(87) PCT Pub. No.: WO2018/232171
PCT Pub. Date: Dec. 20, 2018

(65) Prior Publication Data
US 2021/0145697 A1 May 20, 2021

Related U.S. Application Data

(60) Provisional application No. 62/571,419, filed on Oct. 12, 2017, provisional application No. 62/520,335, filed on Jun. 15, 2017.

(51) Int. Cl.
*A61J 1/20* (2006.01)
*A61J 1/14* (2006.01)

(52) U.S. Cl.
CPC .......... *A61J 1/2096* (2013.01); *A61J 1/1493* (2013.01); *A61J 1/2055* (2015.05); *A61J 1/2062* (2015.05)

(58) Field of Classification Search
CPC ....... A61J 1/2096; A61J 1/2055; A61J 1/1493
See application file for complete search history.

(56) References Cited

U.S. PATENT DOCUMENTS

2007/0088252 A1* 4/2007 Pestotnik ............ A61M 39/223
604/82
2009/0163865 A1 6/2009 Hines et al.
(Continued)

FOREIGN PATENT DOCUMENTS

EP 2303362 B1 6/2019
JP 2015-509421 A 3/2015
(Continued)

OTHER PUBLICATIONS

Notification of Reasons for Refusal, counterpart Japanese App. No. 2019-568677, with English translation (dated Nov. 9, 2021) (12 pages).
(Continued)

*Primary Examiner* — Jason K Niesz
(74) *Attorney, Agent, or Firm* — Cook Alex Ltd.

(57) ABSTRACT

A disposable transfer device has an injection device support surface for receiving an on-body injection device thereon and a flow path arrangement for transfer of fluid into the injection device, the transfer device being configured to define preferential gripping areas for user gripping of an injection device when such device is located on the support surface and interfering areas for interfering with user gripping of the injection device in the interfering areas.

12 Claims, 36 Drawing Sheets

(56) References Cited

U.S. PATENT DOCUMENTS

2010/0305507 A1* 12/2010 Duncan ............... A61M 5/1456
                                                    604/121
2015/0151041 A1   6/2015 Yodfat et al.
2016/0271382 A1   9/2016 Montalvo et al.
2017/0196771 A1*  7/2017 Hooven ............... A61M 5/1782

FOREIGN PATENT DOCUMENTS

| JP | 2016-524513 A | 8/2016 |
| WO | 2014204894 A2 | 12/2014 |
| WO | 2015003145 A1 | 1/2015 |
| WO | 2017014847 A1 | 1/2017 |

OTHER PUBLICATIONS

International Search Report and Written Opinion of the ISA for PCT Application No. PCT/US2018/037624, dated Oct. 4, 2018 (9 pages).
Extended European Search Report Issued by the European Patent Office for Application No. EP18818127.5, dated Feb. 26, 2021 (7 Pages).

* cited by examiner

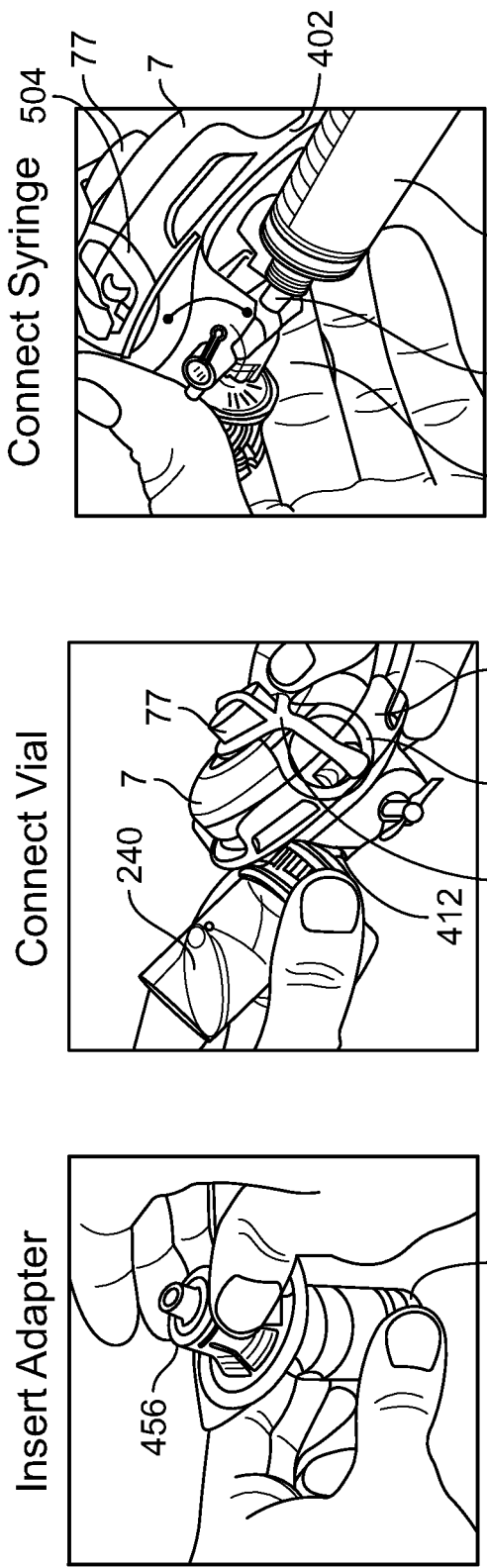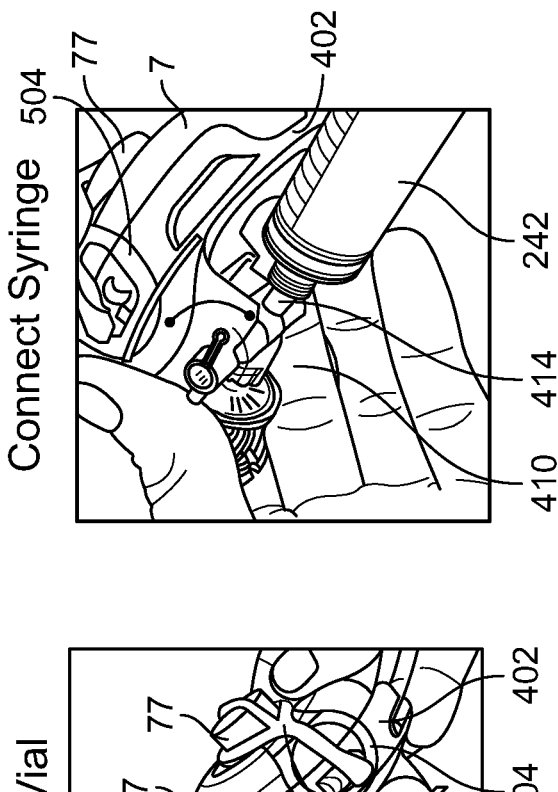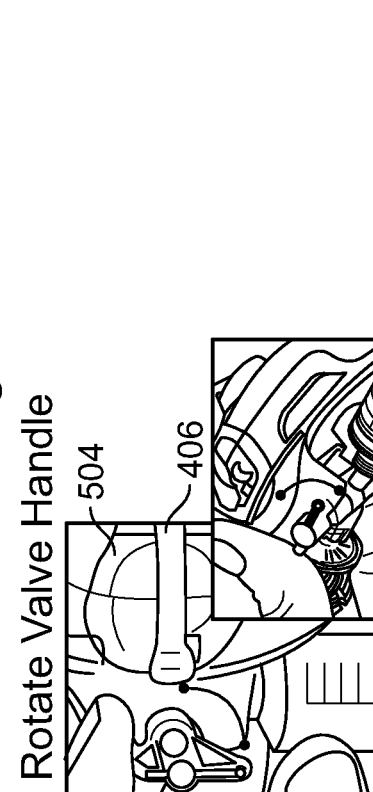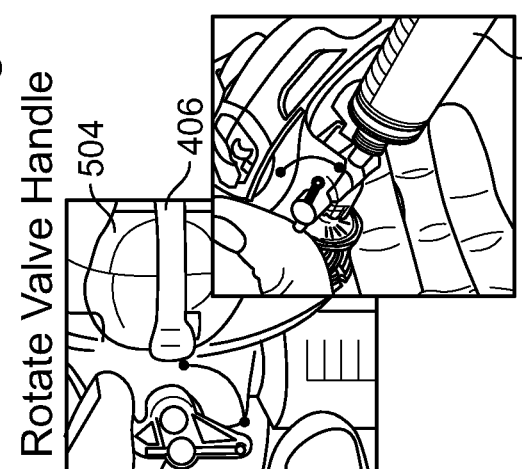

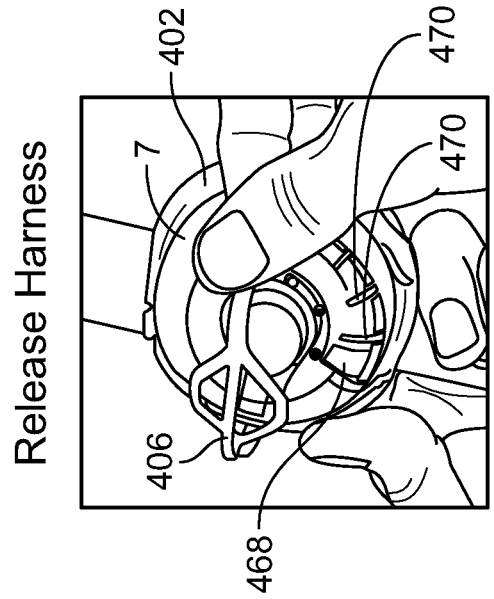
Figure 53H — Release Harness
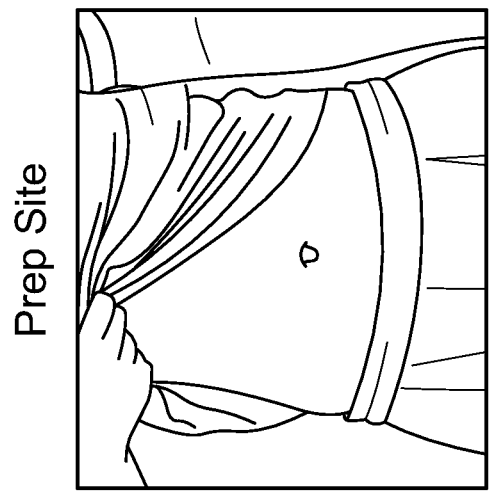
Figure 53G — Prep Site
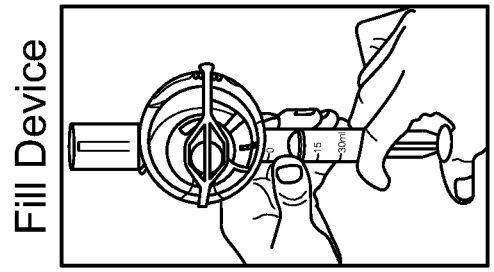
Figure 53F — Fill Device
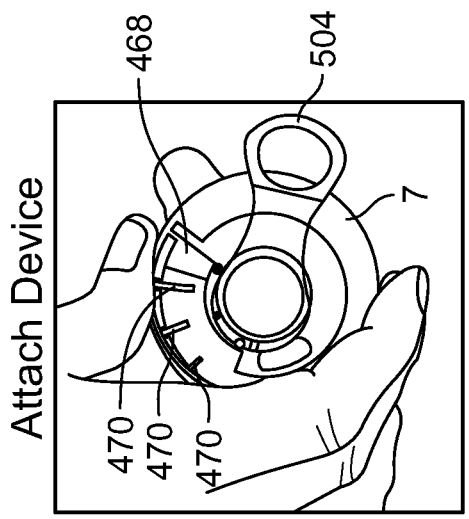
Figure 53J — Attach Device
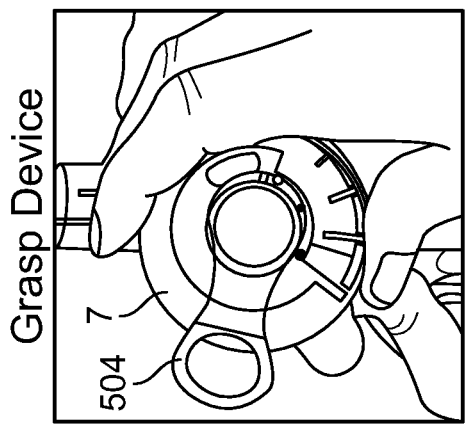
Figure 53I — Grasp Device

HAND-HELD FLUID TRANSFER DEVICE AND SYSTEM

This application is the U.S. National Stage of PCT International Patent Application No. PCT/US2018/037624, filed Jun. 14, 2018, which claims priority to and the benefit of U.S. Provisional Patent Application No. 62/520,335, filed Jun. 15, 2017, and U.S. Provisional Patent Application No. 62/571,419, filed Oct. 12, 2017, the contents of both of which are hereby incorporated by reference in their entirety.

The present subject matter relates generally to a portable transfer device or module for transferring liquid medication from a source vial to an injection device and/or for mixing, diluting or reconstituting a medication and transferring the resulting liquid medication into an injection device.

BACKGROUND

Injection devices that are worn by a patient temporarily or for an extended period are well known in the medical field. The subject matter of this application relates to a transfer device for use particularly but not exclusively with the injection device described in PCT Published Application No. WO 2014/204894, published Dec. 24, 2014, and which is hereby incorporated by reference in its entirety. That injection device includes an internal resilient bladder that may be filled with any suitable injectable medicament, whether drug, antibiotic, biologic or other injectable, for subcutaneous injection, typically a bolus injection, into a patient while the device is being worn by the patient.

This injection device must be filled (wholly or partially) with the desired injectable before injection into the patient. The above PCT published application also discloses a variety of transfer devices for transferring an injectable into the injection device from a source such as a vial or vials. In some situations, the injectable must be diluted or reconstituted, and various devices are disclosed in the above application for accomplishing that. The present application discloses additional novel designs and improvements, allowing lower cost of manufacture and less waste to dispose, for such transfer devices for transferring, diluting and/or reconstituting. The transfer devices described herein may be variously referred to as transfer modules, accessories, add-ons or by other suitable terminology, without intending any limitation on the structure or function of the device not set forth herein.

BRIEF DESCRIPTION OF DRAWINGS

FIG. 51B is a perspective exploded view of the valve subassembly of FIG. 51a.

DESCRIPTION

Injection Device

Figure 1:
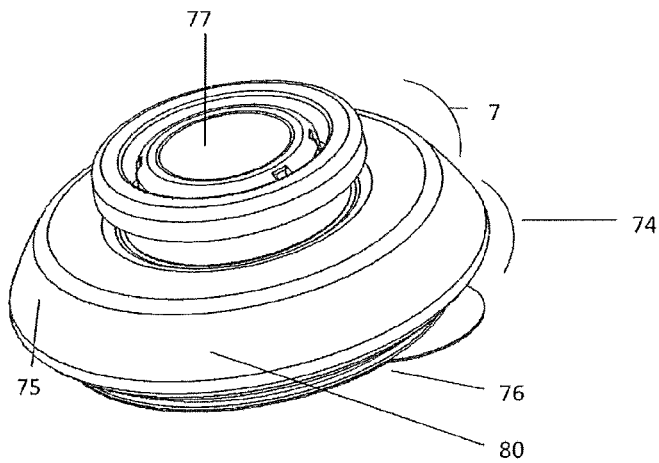
FIG. 1 is a perspective view of the injection device.
Figure 2:
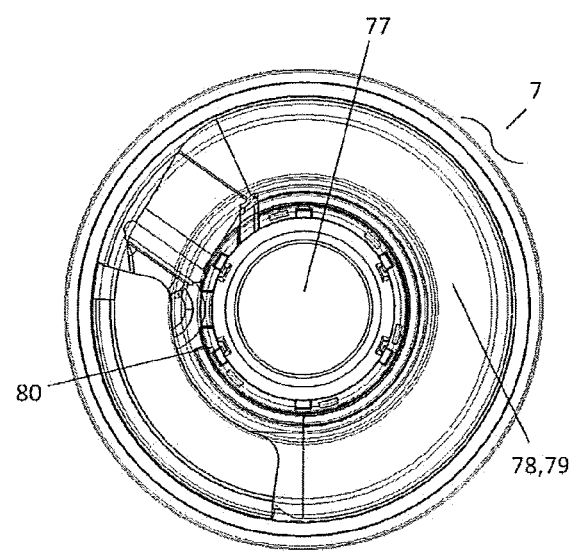
FIG. 2 is a top view of a filled injection device showing the delivery indicator in a full state.
Figure 3:
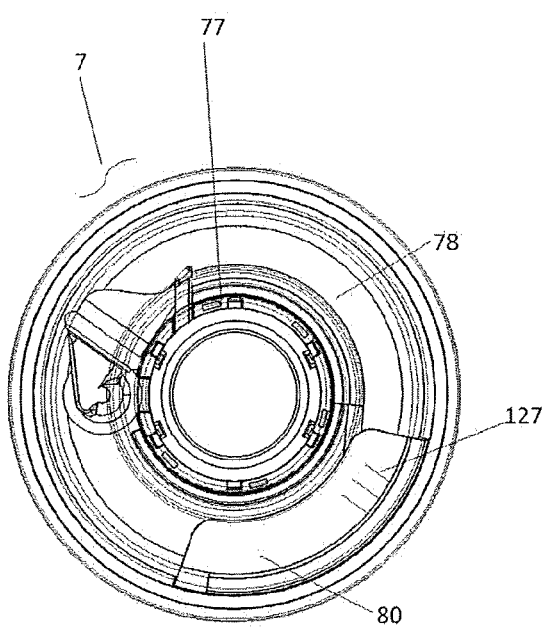
FIG. 3 is top view of a filled injection device showing the delivery indicator in an empty state.

FIGS. 1-20 of this application and the related description extending from this paragraph to the section entitled "Transfer Device" are largely taken from prior published PCT Application No. WO 2014/204894 A2, which is hereby incorporated by reference herein in its entirety. Referring to FIGS. 1-3, the injection device 7 may be of any suitable configuration, but as illustrated it has a generally low-profile, disc shaped outer housing 74 with an upper surface 75 and a lower surface 76, through which an injection needle or cannula protrudes when actuated by the user. The upper surface 75 has an actuator or button 77 to start the injection and a clear section 80 of the housing 74 that allows the subject or medical professional to view the expandable member 78 to ascertain the amount of injectable fluid 79 in the device 7. For example, the user could determine whether the injection has commenced or concluded. More preferably, the expandable member 78 and/or the clear section 80 of the housing 74 may be graduated, such as by line markings 127 or the like, so that the patient or medical professional can visually determine the amount of injectable fluid 79 remaining with greater precision—such as, for example, about 50% complete or about 75% complete. In addition, the expandable member 78 may itself include or interact with a feature on the outer housing 74 to show the amount of injectable fluid 79 remaining. It should be noted that "injectable fluid," "injectable," "drug," "medicament" and like terms are used interchangeably herein. For example, when the injection device 7 is full of drug 79, the clear section 80 may show one color such as but not limited to green. When the injection device 7 is empty of drug 79, the clear section 80 may show a different color such as but not limited to red. In the middle of dispense, the clear section 80 could show a combination of colors.

Figure 4:
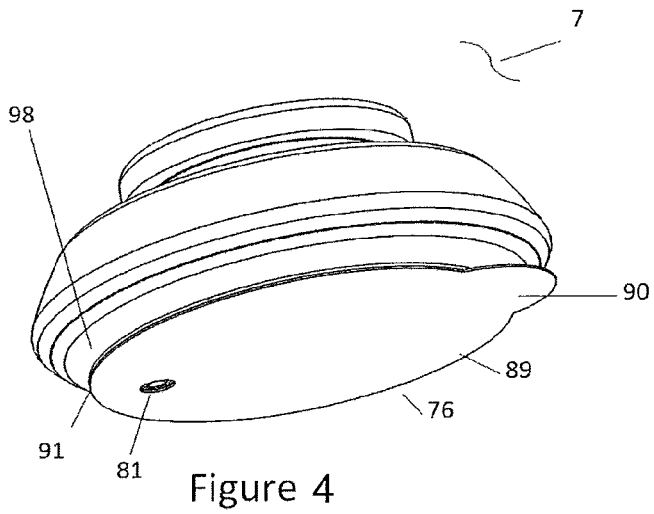
FIG. 4 is a perspective view showing the underside of the injection device with attached tape and fill port.
Figure 5:
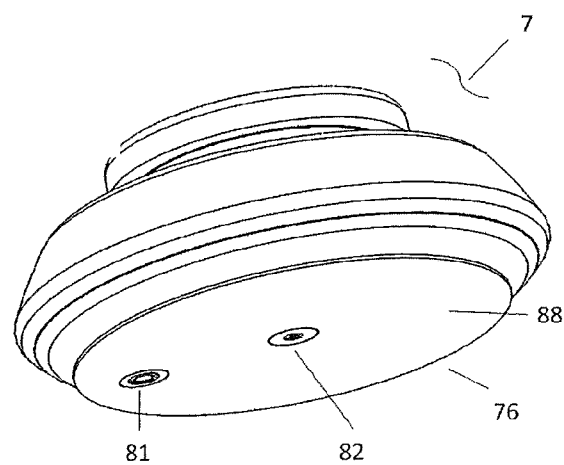
FIG. 5 is a perspective view showing the underside of the injection device with tape detached and the fill and dispense ports exposed.
Figure 6:
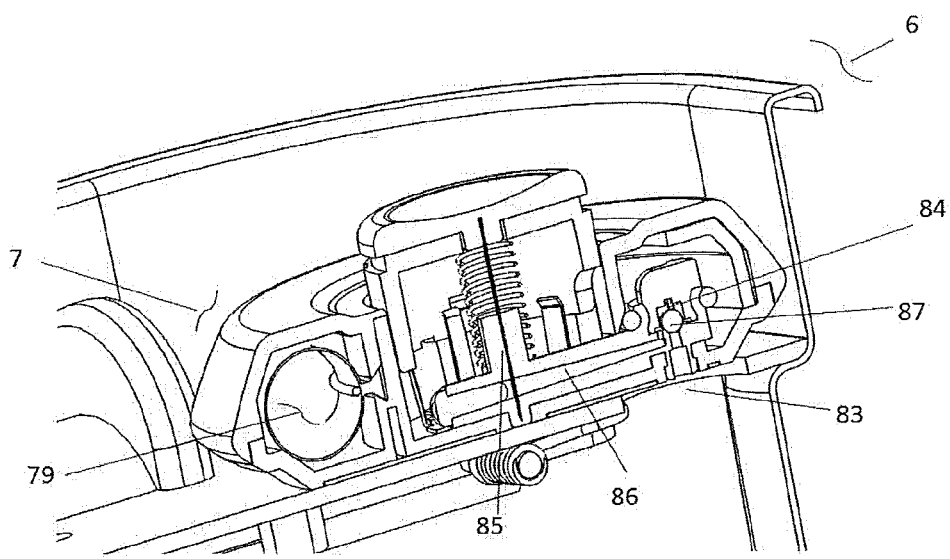
FIG. 6 is a cross-section of the injection device on the transfer apparatus.

Referring to FIGS. 4-6, the undersurface 76 of the injection device 7 includes a filling port 81 and a dispense port 82. The filling port 81 is the interface that allows the transfer apparatus filling tube 83 to transfer liquid 79 to the injection device 7. The dispense port 82 also contains an internal pathway 84 between the expelled injectable 79 from the expandable member 78 and the needle 85. The filling port 81 and dispense port 79 may be in direct fluid communication through internal pathways 86, or they may be combined into a single port.

Referring to FIGS. 4-6, the injection device may preferably include a filling port 81 that includes a check valve 87 to prevent pressurized injectable 79 from leaking out of the injection device 7 when the injection device 7 is removed from the transfer apparatus 6 and the filling port 81 is removed from the filling tube 83.

Referring to FIGS. 4-6, the injection device 7 may also have a filling port 81 that is configured to accept the insertion of a syringe. This syringe may be configured with a luer fitting or a needle. This filling port 81 configuration allows for the manual filling of the injection device by the user. The transfer apparatus 6 may still be used but would not be required in this configuration.

Referring to FIGS. 4-6, the injection device 7 may also have a dispense port 82 that is configured to directly connect to an intravenous cannula via attached tubing or a standard needle port.

Referring to FIGS. 4-6, the undersurface 76 of the injection device 7 carries an adhesive 88 for securing the injection device 7 temporarily to the skin of a subject until the injection is complete. During removal of the injection device 7, an adhesive tape liner 89 may be removed automatically exposing the adhesive surface 88 on the undersurface 76 of the injection device 7 that may be used to adhere the injection device 7 to the patient's skin. Alternatively, the tape liner 89 may have a tab 90 that the user pulls to manually remove before adhering the injection device 7 to the skin. Alternatively, this tab may be attached to the surface of the transfer device 4 so that the tape liner is automatically removed upon removal of the injection device 7.

Referring to FIGS. 4-6, the injection device 7 may have an adhesive tape flange 91 that extends beyond the undersurface base 76. This flange 91 of adhesive tape 88 can act as a strain relief between the injection device 7 and skin surface, reducing the risk of accidentally dislodging the injection device 7 from the skin. In other words, similar to a tapered strain relief on a wire where it enters into a connector, the extended adhesive flange 91 acts to distribute the load on both sides of the connection point between the adhesive tape 88 and the undersurface base 76 of the injection device 7 to reduce any stress risers at the adhesive tape 88 and skin interface.

Referring to FIGS. 4-6, the injection device 7 may be configured with a tapered underside surface 98 that presses on the adhesive flange 91 to securely attach the adhesive tape 88 to the skin as the user is securing the injection device 7 to the skin without additional user intervention. By using the compliance of a person's skin when pressing the injection device 7 against the skin, the tapered underside surface 98 of the injection device 7 effectively presses the flange 91 of the adhesive tape 88 against the skin but the upper exposed surface of the flange 91 portion does not have exposed adhesive and therefore is not attached to that portion of the tapered underside surface 98. The user is not required to run their finger around the flange 91 to secure the injection device 7 to the skin making it a much simpler method of adhesive tape 88 attachment.

Referring to FIGS. 4-6, the injection device 7 may have an underside surface 76 that is flexible or compliant in lieu of being rigid to allow for improved attachment by conforming of the injection device 7 to the skin during application.

Figure 7:
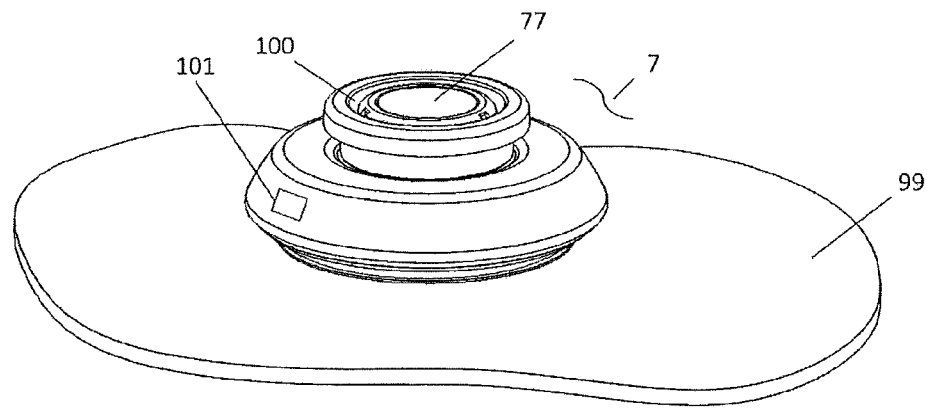
FIG. 7 is a perspective view of the injection device attached to the skin with the safety device installed.
Figure 8:
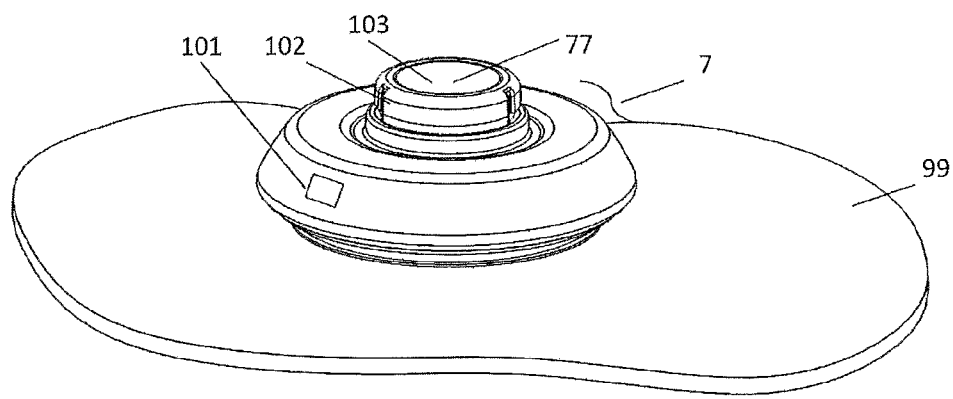
FIG. 8 is a perspective view of the injection device attached to the skin with the safety device removed and the button up in a pre-fire state.
Figure 9:
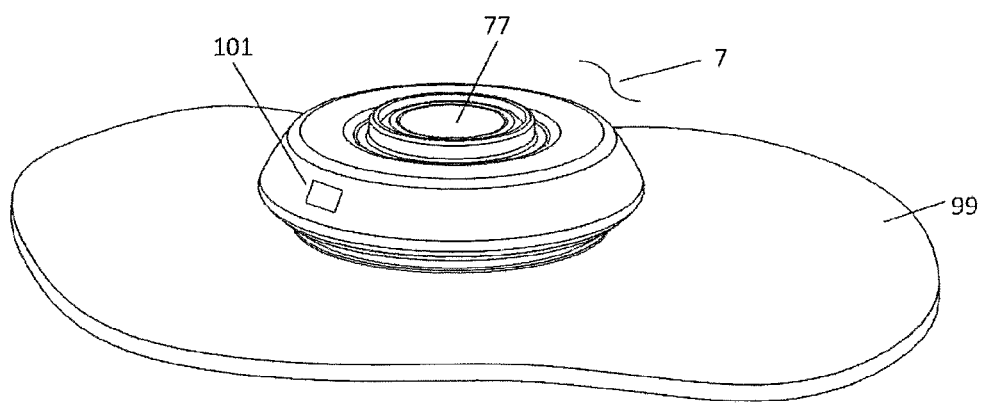
FIG. 9 is a perspective view of the injection device attached to the skin with the safety device removed and the button down in a fired state.

Referring to FIGS. 7-9, after the injection device 7 is placed against or adhered to the skin 99, a safety mechanism or lock-out mechanism may be automatically released and the injection device 7 is ready to fire (inject). In other words, the injection device 7 is prevented from being actuated (it is locked out) until it is placed against the skin. Alternatively, the user may manually remove a safety 100 such as a safety pin, safety sleeve, or collar to release the injection device to be ready to fire (inject). The injection device 7 preferably cannot be fired until the safety mechanism 100 is released. The safety mechanism 100 may be passive or active and manually triggered by the user or automatically triggered by the injection device 7.

Referring to FIGS. 7-9, the injection device 7 may use an actuator or button 77 and a visual indicator 101 in combination to define the state of the injection device 7 after it has been removed from the transfer apparatus. For example, when the button 77 is in the up position and the indicator 101 has one color such as but not limited to green, this may indicate that the injection device 7 is ready to start the injection. Additionally, the button 77 may have a side wall 102 that is a different color from its top 103. When the button 77 is depressed, the user cannot see the sidewall 102 of the button 77; this may indicate that the injection device 7 is in use. The injection device 7 may alert the user when the injection of the drug is completed. This alert could be in the form of visual indicators, audible sounds, mechanical movements or a combination. The button 77 is ideally designed to give the user audible, visual and tactile feedback when the button 77 'pops up' into the locked-out position. The injection device 7 may indicate to the user that it is has completed dispensing and the full dose has been delivered to the patient with the button 77 in the up position and indicator window 101 showing the injection device is empty. For example, when the button 77 is in the up position and indicator 101 shows a different color such as but not limited to red, this may indicate that the injection device 7 has completed the injection.

Figure 10:
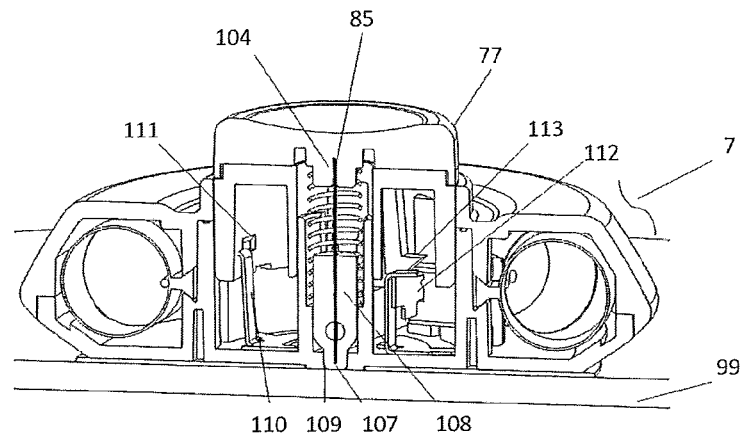
FIG. 10 is a cross-section view of the injection device attached to the skin with the button up in a pre-fire state.
Figure 11:
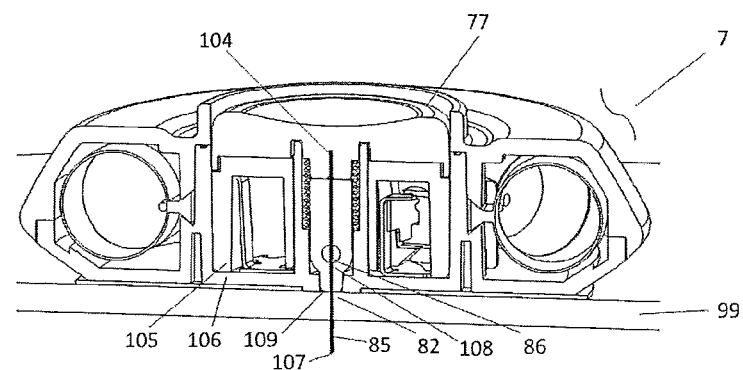
FIG. 11 is a cross-section view of the injection device attached to the skin with button down in a first fired state.
Figure 12:
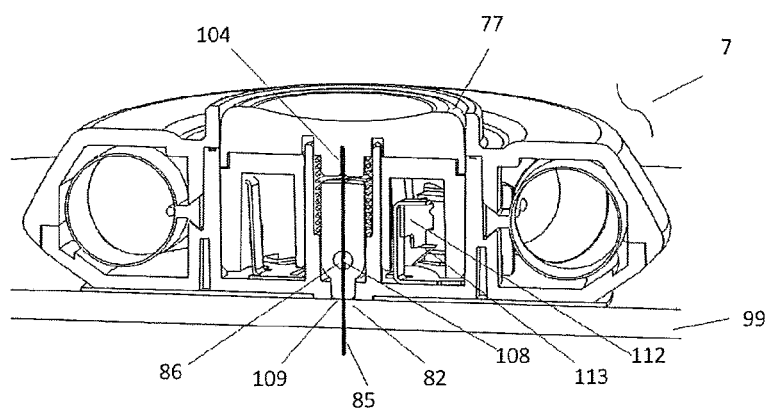
FIG. 12 is a cross-section view of the injection device attached to the skin with button down in a dispense state.

Referring to FIGS. 10-12, the injection device 7 may have an actuator or button 77 that the user depresses on the injection device 7 to start the injection. The button 77 may be configured to be an on/off switch, i.e., to only have two states, open and closed such as a light switch. This may prevent the user from pushing the button 77 halfway and not actuating the injection device 7. Once activated, this 'light switch' type button 77 would insert the needle 85 rapidly into the skin 99, independent of the user manipulation of the button 77. Alternatively, the button 77 could have a continuous motion, allowing the user to slowly insert the needle 85 into skin 99. The button 77 may preferably be directly coupled to the needle 85 by using adhesive 104 creating a button 77 and needle 85.

Referring to FIGS. 10-12, the injection device 7 may have a needle 85 travel into the skin 99, upon actuation of the button 77 that initially goes to a first position or depth as shown in FIG. 11 and retracts slightly to a second position of depth preferably automatically as shown in FIG. 12. The first depth shown in FIG. 11 is achieved from over travel of the button 77 during actuation. The first depth may be controlled by features 105 in the button 77 in direct contact with the base 106 of the injection device 7. The final depth of the needle 85 is suitable for subcutaneous injections. Alternatively, the final depth of the needle 85 may be reduced for intradermal injections. Alternatively, the final depth of the needle 85 may be increased for intramuscular injections. Upon reaching the first depth, the needle 85 retracts back to a second depth as shown in FIG. 12. The retraction distance of the needle to the second depth is in the range of 0.1-2 mm. This retraction feature is preferable to prevent the needle 85 from being blocked by tissue during the initial insertion process. This tissue blockage could require a very high pressure to overcome and prevent the injection device 7 from delivering the drug. The retraction of the needle 85 from the first position to a second position creates an open pocket ahead of the needle tip 107 allowing reduced pressure for initiation of flow of drug from the needle 85. This reduced pressure for initiation of the flow of drug from the needle is preferable for the injection device 7 to maintain a relatively constant pressure during injection.

Referring to FIGS. 10-12, the injection device 7 may include a needle 85 with a side hole 108. As shown in FIG. 12, once the button 77 on the injection device 7 is fully depressed, the needle 85 will be fully inserted into the skin 99 through the dispense port 82 and the injection device 7 will begin dispensing of the injectable. Until the button 77 is fully depressed, the side-hole 108 and therefore the internal lumen of the needle 85 is not in communication with the fluid channel 86 of the dispense port 82. Both the side-hole 108 and needle-tip 107 are retained within a septum 109. With the side-hole 108 and needle-tip 107 being retained within the septum 109, the entire drug path is kept sterile until the time of use. When the button 77 is fully depressed and the needle 85 is in the dispense position, a side hole 108 in the needle 85 is in communication with the fluid channel 86 of the dispense port 82 and the injection of the liquid begins.

Referring to FIGS. 10-12, the septum 109 provides the advantage of sealing the needle tip 107 as well as the side hole 108 from the injectable before and after dispense. Sealing the needle tip 107 and the side hole 108 of the needle 85 at the end of the injection has a particular advantage to prevent dripping of injectable from the injection device 7 after end of dispense and/or after it is removed from the skin surface. It also prevents contaminants from entering the hollow needle prior to being actuated into the skin. The septum 109 may be made of any suitable material to allow for sealing once the needle 85 has punctured it. The material composition of septum 109 may preferably be silicone. Alternatively, the material composition of the septum may also be a blend of different materials including but not limited to bromobutyl, chlorobutyl, isoprene, polyisoprene, SBR, polybudtadiene, EPDM, natural rubber and silicone. Alternatively, the fluid pathway 86 including the dispense port 82 could be a rigid plastic with a silicone injected over mold to produce the septum previously described.

Referring to FIGS. 10-12, the septum 109 at the dispense port 82 could protrude slightly from the underneath surface of the injection device 7 into the skin surface 99 to provide for pressure on the skin surface 99 at the injection site. This pressure on the skin surface 99 by the dispense port 82 after the needle is retracted could eliminate injectable from coming out of the injection site, commonly referred to as blowback.

Referring to FIGS. 10-12, the injection device 7 may include a set of spring tabs 110 that interface with the button 77 to perform locking functions. A spring tab 110 is biased to lock into an undercut 111 in the button 77 to keep the button 77 in a first up position or pre-fire position as shown in FIG. 10. The geometry of the undercut 111 and spring tab 110 help to produce the light switch actuation force described previously. This light switch actuation is accomplished by the translation of the button 77 relative to the spring tab 110 and the geometry of the mating undercut 111 surfaces.

Referring to FIGS. 10-12, the injection device 7 may include a spring tab 112 that interacts with the button 77 in the injection device 7 to perform locking functions such that when the button 77 is actuated to the first depth and retracts slightly back to the second depth or dispense position, undercut features 113 in the button 77 allow the spring tab 112 to hold the button 77 in the dispense position until the injection device 7 has completed dispensing.

Figure 13:
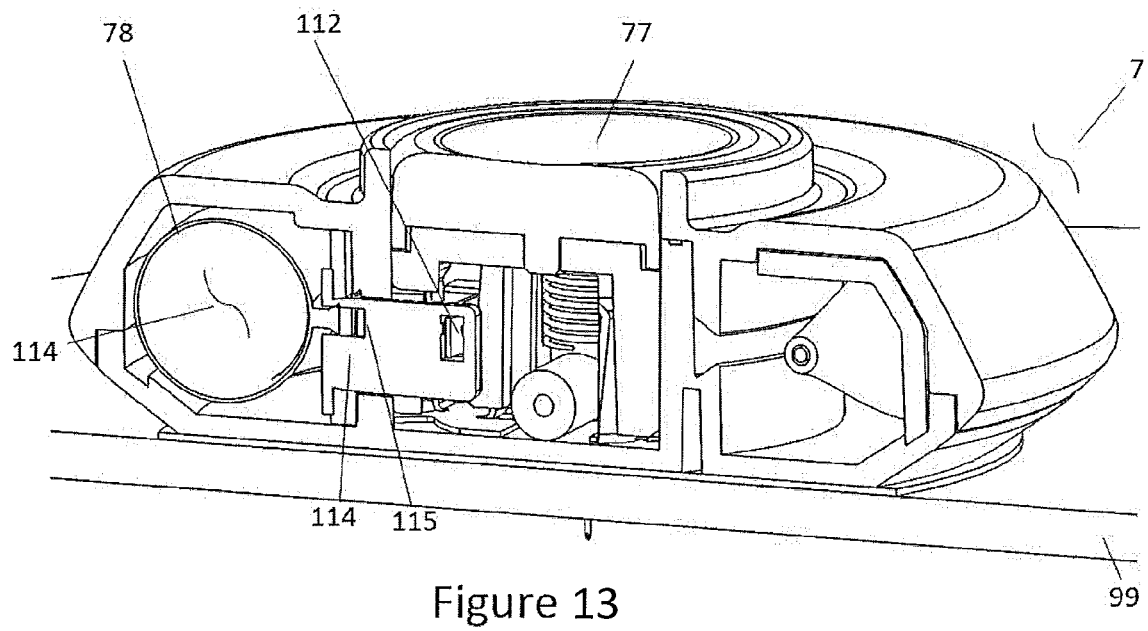
FIG. 13 is a cross-section view of the injection device attached to the skin showing the end of delivery indicator not triggered.
Figure 14:
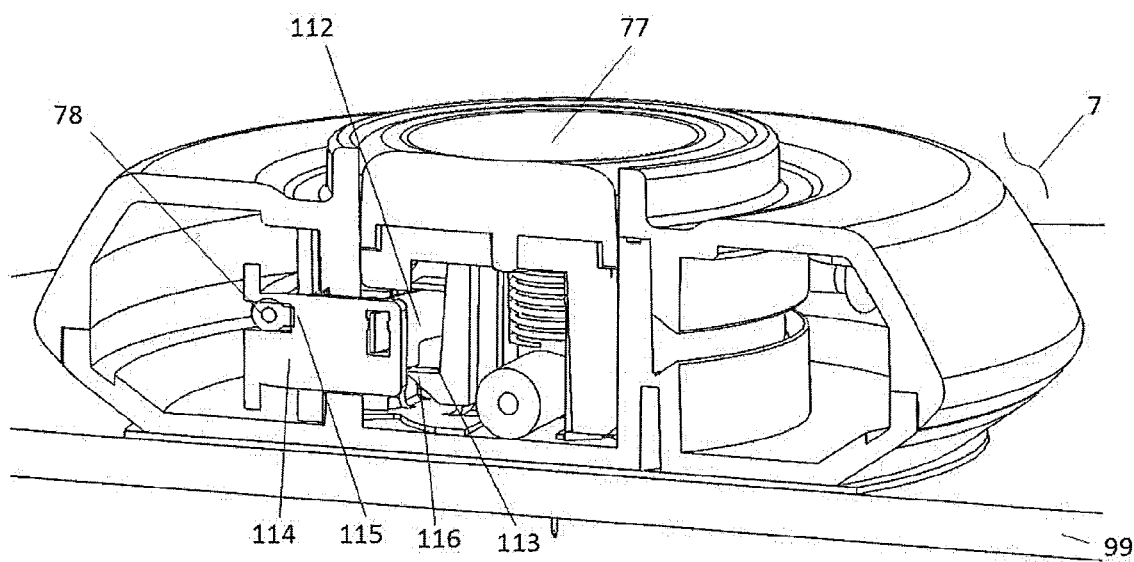
FIG. 14 is a cross-section view of the injection device attached to the skin showing the end of delivery indicator triggered.

Referring to FIGS. 13-14, the injection device 7 may include an end of delivery indication or empty indicator 114 to sense when all of the fluid 79 has been expelled from the expandable member 78 and the injection device 7 has completed dispensing. The empty indicator 114 may be configured with a slot or other opening 115 to slide over the expandable member 78 at the exit port when the expandable member 78 is in a deflated state after all of the fluid has been expelled. There may be two states of the empty indicator. As shown in FIG. 13, the empty indicator may be in a first position or deflected-out state when the expandable member 78 is full with fluid 79 at that section and is not contained within the slot or opening 115. This first position would translate to a non-empty state of the expandable member 78 when the diameter of the expandable member 78 is larger than its minimum due to residual fluid 79 contained within. As shown in FIG. 14, the empty indicator 114 may be in a second position or deflected-in state when the expandable member 78 is partially or fully contained within the slot or opening 115. This second position would translate to an empty state of the expandable member 78 when the diameter is at a minimum.

Referring to FIGS. 13-14, the injection device 7 may include an automatic needle retraction mechanism at the end of dispense. This mechanism includes a direct coupling between a spring tab 112, button undercut feature 113 and the empty indicator 114, all previously mentioned. When the expandable member 78 is filled with injectable 79 and the button 77 is depressed from a first pre-fire position to a second dispense position as shown in FIG. 14, undercut features 113 in the button 77 allow a spring tab 112 to hold the button 77 in the dispense position until the injection device 7 has completed dispensing. This spring tab 112 may also be directly coupled to the empty indicator 114 which is naturally in the first position or deflected-out state. The motion of depressing the button 77 to a second position or dispense position allows a post feature 116 in the button 77 to provide a bias or pre-tension on the spring tab 112 to urge the empty indicator 114 to its second position or deflected-in state. However, since the expandable member 78 is initially full with injectable 79 at a large diameter, the empty indicator 114 cannot move to the second position or deflected-out state as shown in FIG. 13. After the button 77 is depressed, the fluid 79 starts to expel out of the expandable member 78 through the needle as previously mentioned. Once the expandable member 78 has expelled all of the fluid 79 and is at a minimum diameter, the empty indicator 114 (under pretension from the spring tab 112) will move to the second position or deflected-in state as shown in FIG. 14. The spring tab 112 directly coupled to the empty indicator 114 also moves with the empty indicator 114. This movement releases the spring tab 112 from the undercut feature 113 in the button 77 to allow the button 77 (and needle) to move up to a final position or post fire position after the dispense is completed as shown in FIG. 15.

Figure 15:
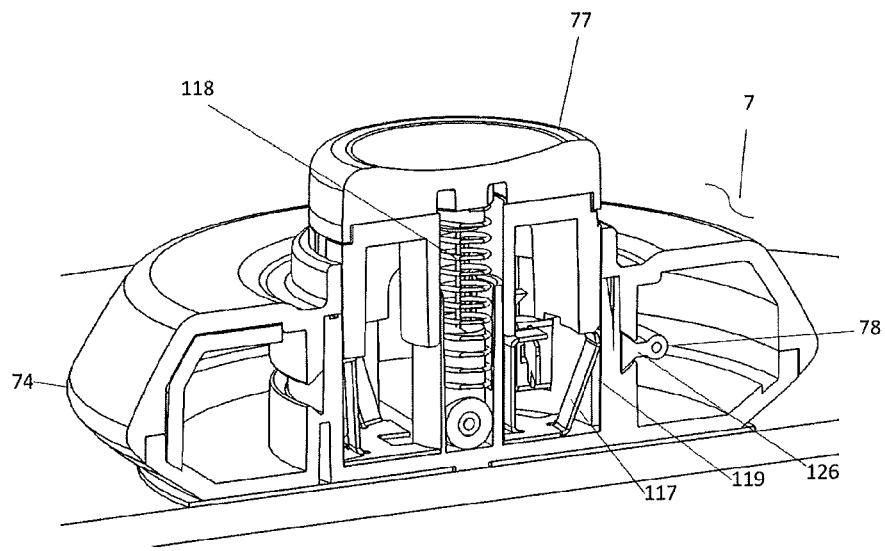
FIG. 15 is a cross-section view of the injection device attached to the skin with button locked up in a post-fired state.

Referring to FIG. 15, lock out spring tabs 117 may also interact with the button 77 in the injection device 7 to perform locking functions such that when the injection is complete the button 77 is released, and the button 77 is urged up by the return spring 118 to a final up position or post-fire position. The button height 77 relative to the top of the injection device 7 in the final up position or post-fire position (shown in FIG. 15) may be higher than the pre-firing position (shown in FIG. 10). The end of the lock out spring tabs 117 move out to the outer diameter surface 119 of the button 77 within the outer housing 74 to lock the button 77 in the up position or post-fire position and prevent the button 77 from being actuated again.

Referring to FIG. 15, the injection device 7 may include a return spring 118 that interacts with the button 77 to provide a bias to the button 77 into a first up position or pre-fire position. When the button is actuated down to a second depth or dispense position, the return spring 118 is compressed causing more of a bias or preload. At the end of the dispense period, the button 77 is unlocked from the second depth or dispense position (shown in FIG. 12) to move up to a final position or post fire position after the dispense is completed as previously mentioned. It is the bias of the return spring 118 that forces the button 77 up to a final position or post-fire position.

Figure 16:
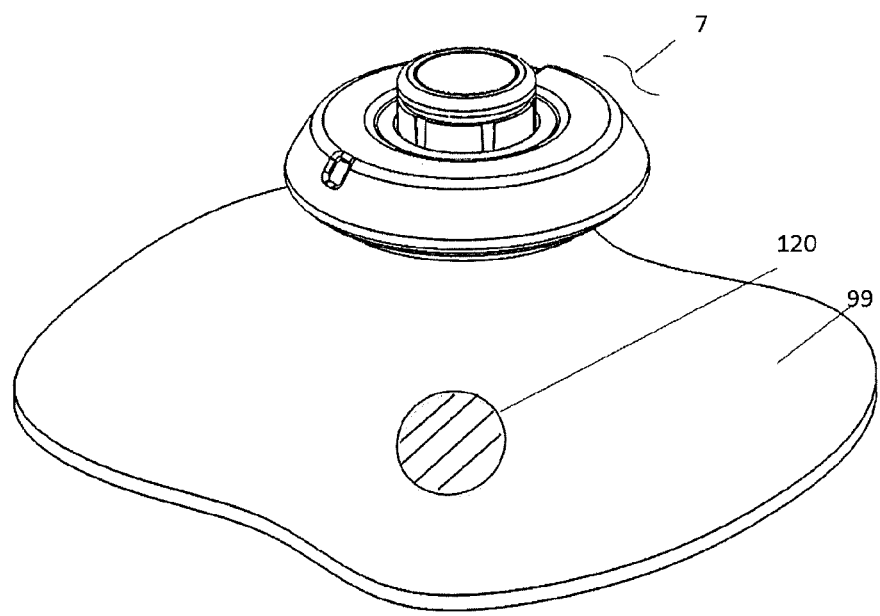
FIG. 16 is a perspective view of the injection device removed from the skin with the bandage remaining on the skin.
Figure 17:
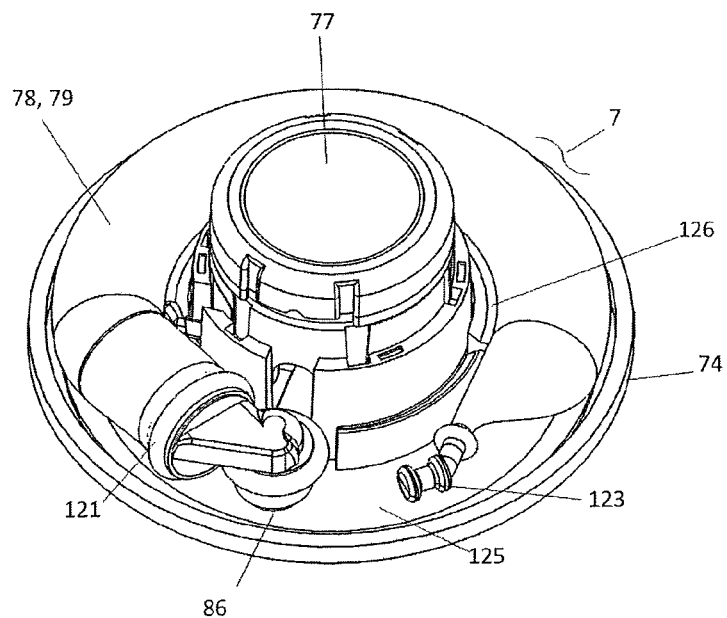
FIG. 17 is a perspective view of the injection device with the top housing removed in a filled state.
Figure 18:
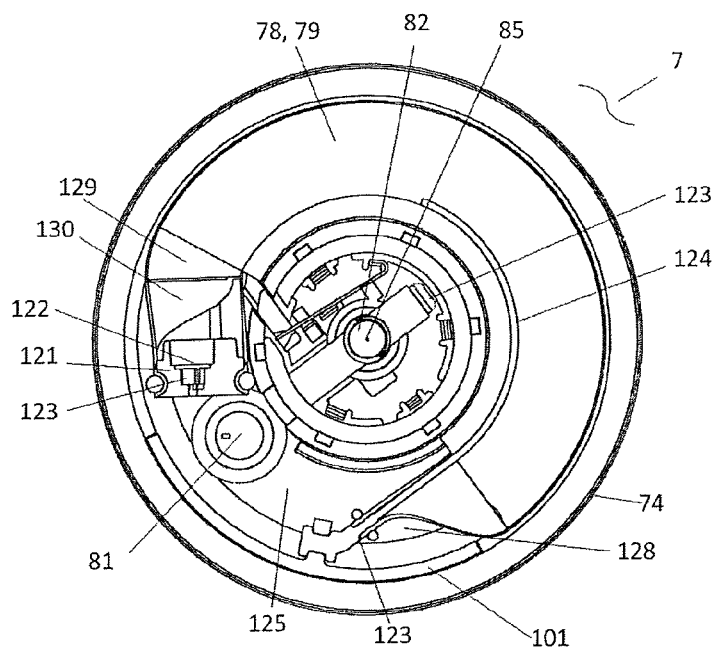
FIG. 18 is a top view of the injection device shown in FIG. 17.
Figure 19:
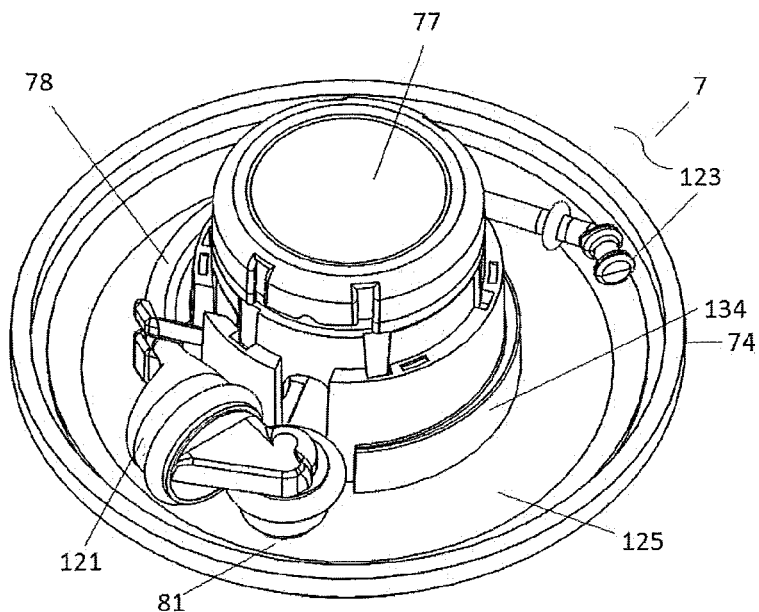
FIG. 19 is a perspective view of the injection device with the top housing removed in an empty state.
Figure 20:
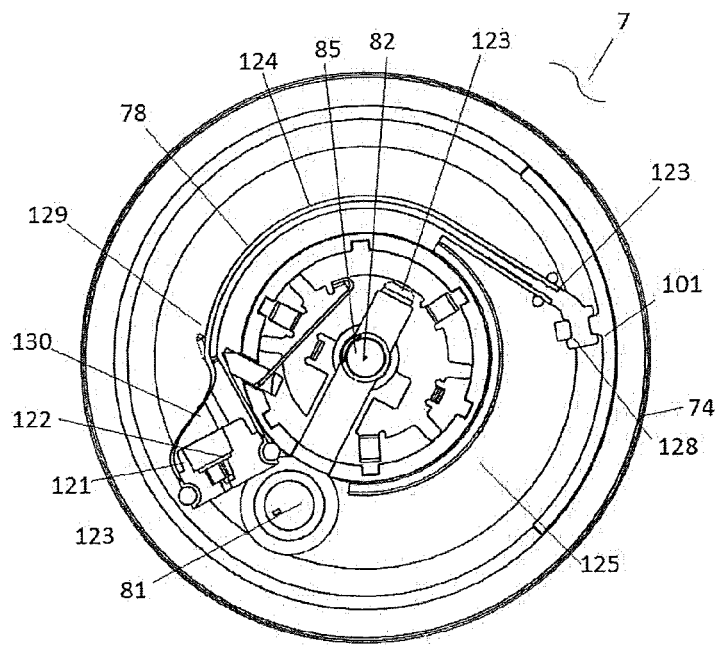
FIG. 20 is a top view of the injection device shown in FIG. 19.
Figure 21:
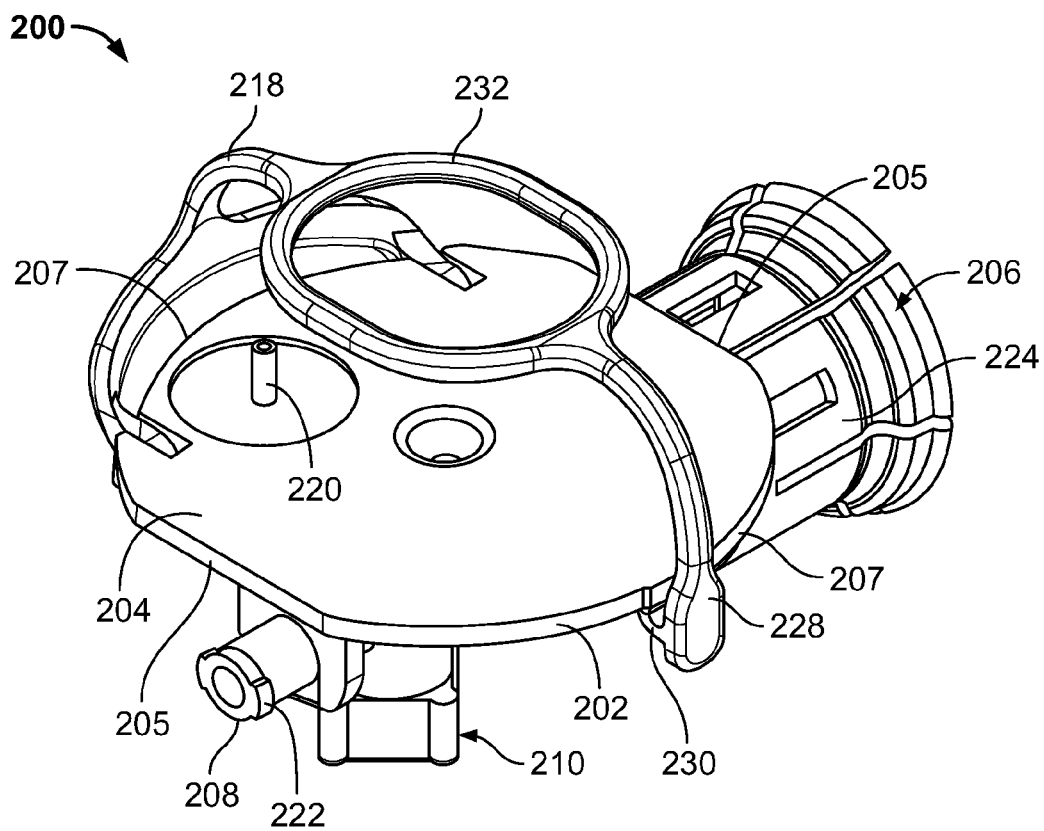
FIG. 21 is a perspective view of a transfer device for temporary coupling to an injection device such as the device shown in the figures above for manipulating/transferring an injectable from a vial into the injection device and a syringe.
Figure 22:
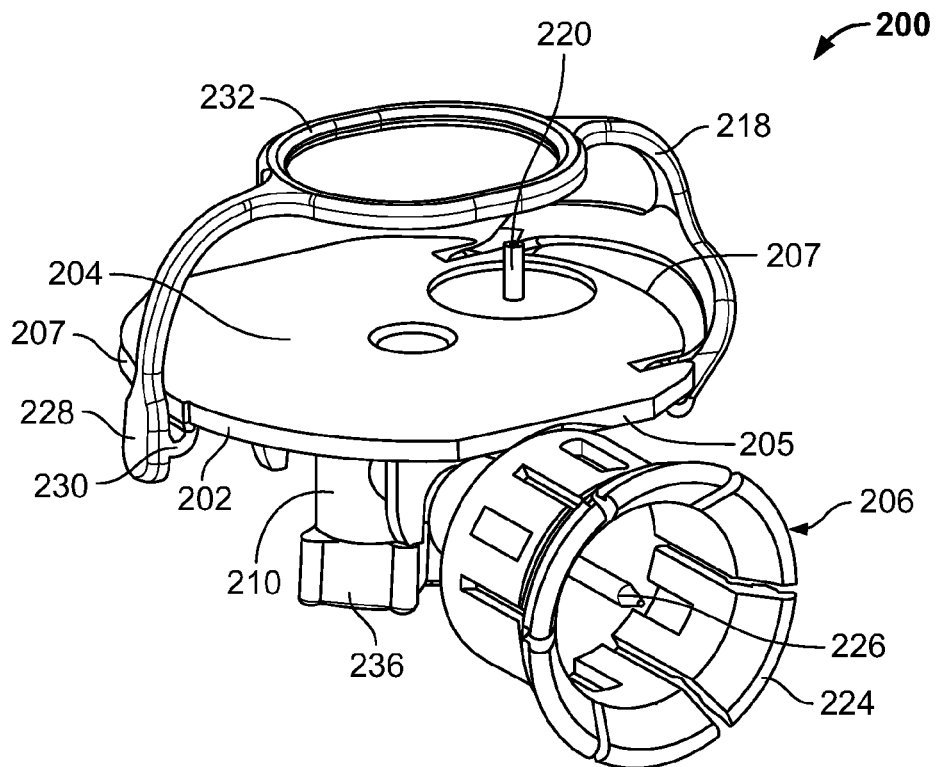
FIG. 22 is a perspective view of the transfer device of FIG. 21, taken from a different angle.
Figure 23:
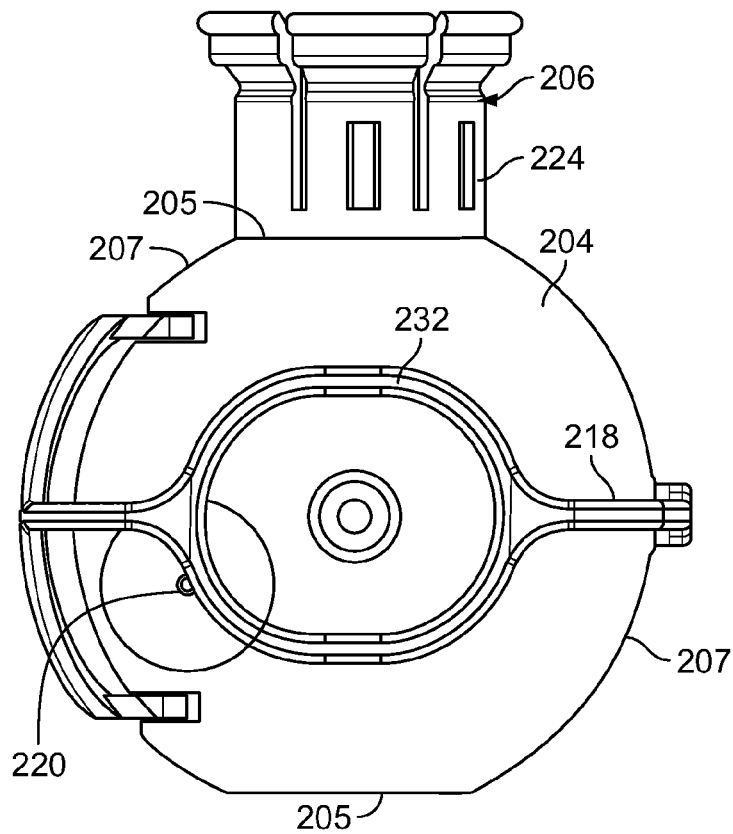
FIG. 23 is a top view of the transfer device of FIG. 21.

Referring to FIG. 15-16, upon removal of the injection device 7 from the skin 99, the injection device 7 will preferably be locked out, preventing non-destructive access to the needle or reuse of the injection device 7. The injection device 7 may indicate to the user that the full dose has been delivered. This indication could be in the form of a visual indictor, audible sound, mechanical movement or a combination.

Referring to FIG. 16, upon removal of the injection device 7 from the skin 99, a bandage 120 may release from the injection device 7 and remain on the skin surface 35. This can be affected by using an adhesive on the bandage portion that more strongly attaches the bandage to the skin than the adhesive that attaches the bandage to the injection device 7. Thus when the housing is lifted from the skin, the bandage 120 remains in place over the injection site as described in U.S. Pat. No. 7,637,891 and U.S. patent application Ser. No. 12/630,996, filed Dec. 4, 2009 incorporated by reference herein.

Referring to FIGS. 17-20, the injection device 7 may preferably include a manifold 121 that assembles to both the expandable member 78 and the filling port 81 and dispensing ports 82, and provides direct fluid communication between the expandable member 78 and the filling 81 and dispensing 82 ports of the injection device 7. The manifold 121 may be configured on the end that assembles to the expandable member 78 to be large in diameter to facilitate filling and expelling all of the fluid 79 out of the expandable member 78 as previously discussed. The manifold 121 may preferably include internal passageways 122 to allow for fluid flow in and out of the expandable member 78.

The manifold 121 may be configured with a filter 123 in the injectable fluid pathway 122 for filtering the injectable 79 to remove particulate before and after it is introduced into the expandable member 78. The filter 123 may be a membrane, depth filter or other suitable filtration media that is of sufficiently small pore size or effective pore size to remove objectionable particulate, which may include but not be limited to undissolved injectable 79 in those situations where the injectable 79 is reconstituted by the transfer apparatus.

The manifold 121 may also be configured with a filter 123 for the removal of air. Such an air remover filter 123 may include a bubble trap, air gap or other configuration in the injectable fluid pathway 122 that removes air from the injectable fluid pathway 122 before it is introduced into the expandable member 78. This air remover filter 123 may be configured with a hydrophobic filter or a combination of hydrophobic and hydrophilic filters. A hydrophobic filter would allow for the venting of air from the transfer apparatus but not the passage of liquid. A hydrophilic filter would allow the passage of liquid but not the passage of particulate or air. The air remover filter 123 may also have check valves to allow for venting of trapped air. Alternately, the air remover and filters 123 may be located at any point in the fluid pathway from the filling port 81 to the needle 85. For example, the most downstream point in the fluid pathway is the distal end 128 of the expandable member 78. An internal mandrel 124 may be connected to distal end 128 of the expandable member 78. An air remover or filter 123 may be integrated into this downstream point to allow for venting of trapped air during filling of the injection device 7. Furthermore, the mandrel 124 could include a slot along its length that is in communication with the downstream filter 123 to aid in the venting of air during the filling process.

Referring to FIGS. 17-20, the injection device 7 may include a resilient expandable member 78 such as an elastomeric balloon or bladder. The material composition of expandable member 78 may preferably be silicone. Alternatively, the material composition of the expandable member 78 may also be a blend of different materials including but not limited to bromobutyl, chlorobutyl, isoprene, polyisoprene, SBR, polybudtadiene, EPDM, natural rubber and silicone. In addition, the expandable member 78 may be coated to improve the surface properties. Coatings may include parylene, silicone, Teflon and fluorine gas treatments. Alternatively, the expandable member 78 may be made from a thermoplastic elastomer.

Referring to FIGS. 17-20, the injection device 7 may include a resilient expandable member 78 to which the injectable 79 is transferred under pressure. This causes the expandable member 78 to enlarge and the resilience of the expandable member 78 creates a pressure which tends to expel the injectable 79. The pressure chamber of the transfer apparatus described previously (or such other pump or pressurizing means as may be employed in the transfer apparatus) transfers the injectable 79 to the injection device 7 under pressure. Introducing the injectable 79 into the expandable member 78 under pressure causes it to stretch and expand both in diameter and length. An example of this would be blowing up a long, skinny balloon. The volume range of the injection device 7 may be 0.5 to 30 milliliter. When expanded, the resilient expandable member 78 exerts an expulsion pressure in the range of 1 to 200 psi on the injectable 79 contained in the expandable member 78 so that the injection device 7 is ready to administer the injectable 79 automatically when triggered by the user by depression of the button as previously described.

Transfer Device

Figure 24:
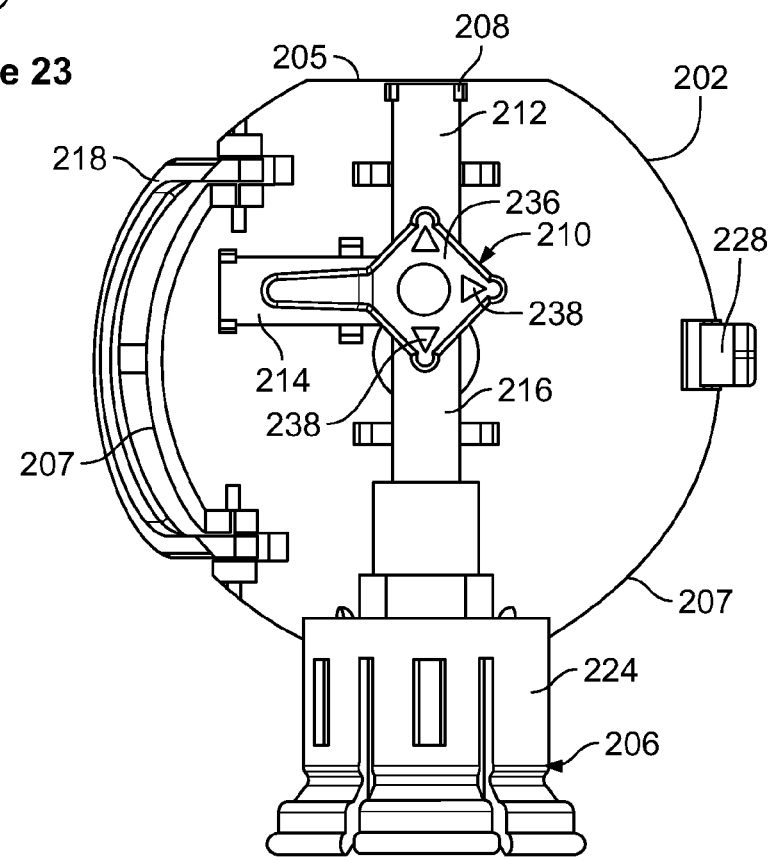
FIG. 24 is a bottom view of the transfer device of FIG. 21.
Figure 25:
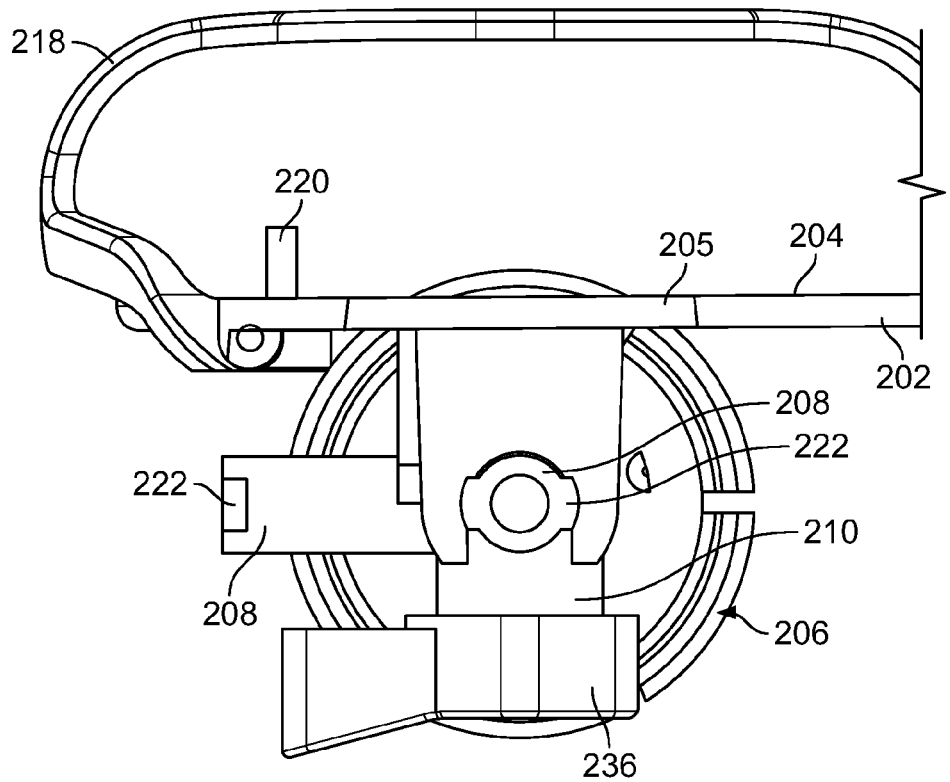
FIG. 25 is an end view of the transfer device of FIG. 21 looking directly at a syringe adapter.
Figure 26:
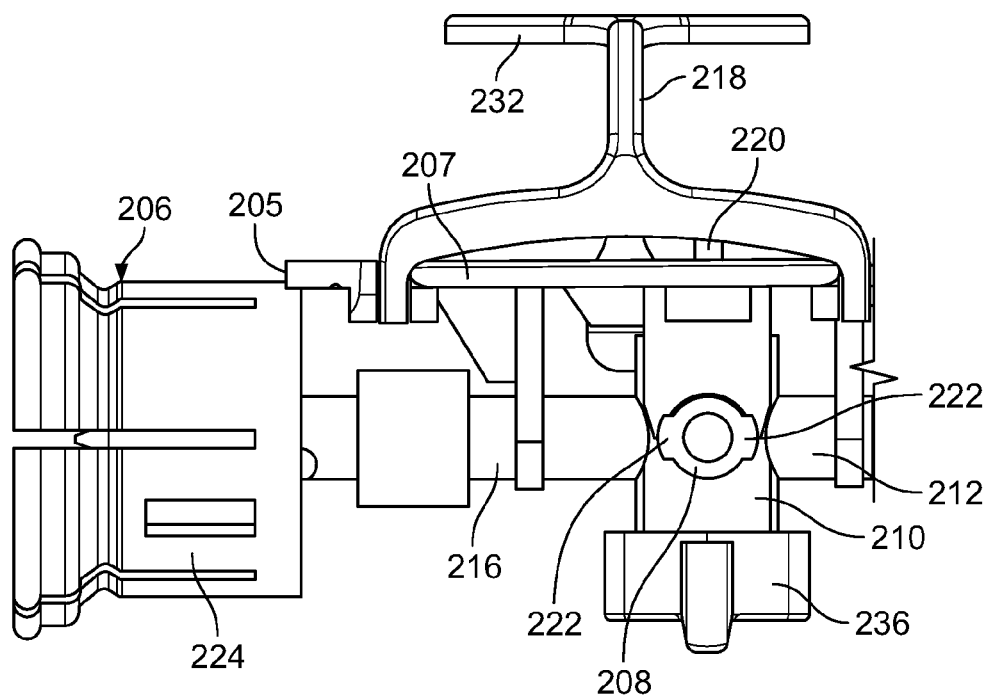
FIG. 26 is a side view of the transfer device of FIG. 21.
Figure 27:
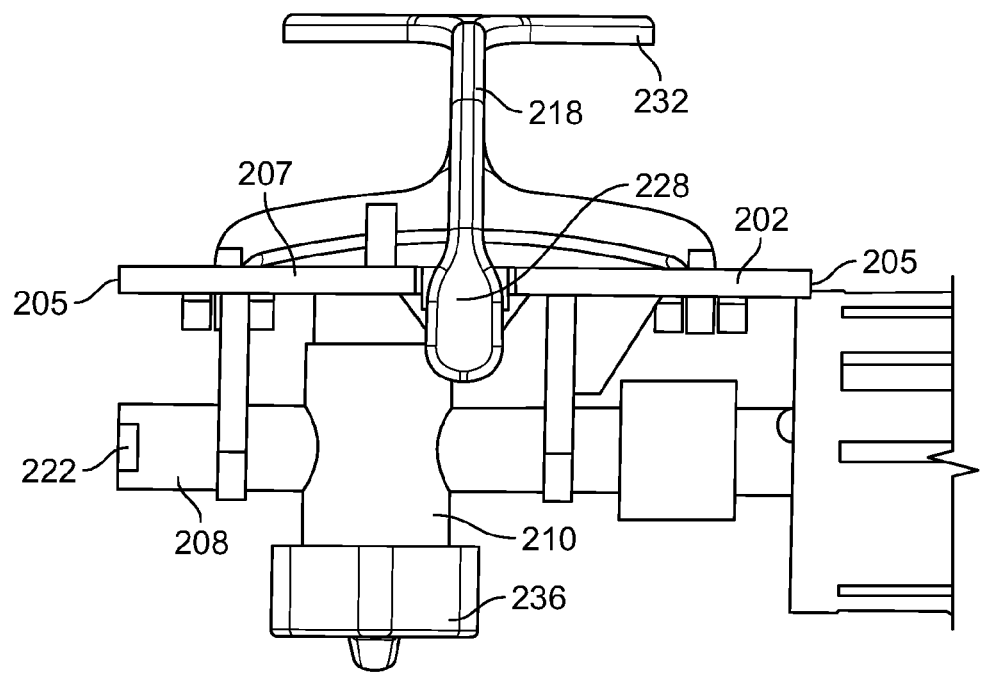
FIG. 27 is an opposite side view of the transfer device of FIG. 21.
Figure 28:
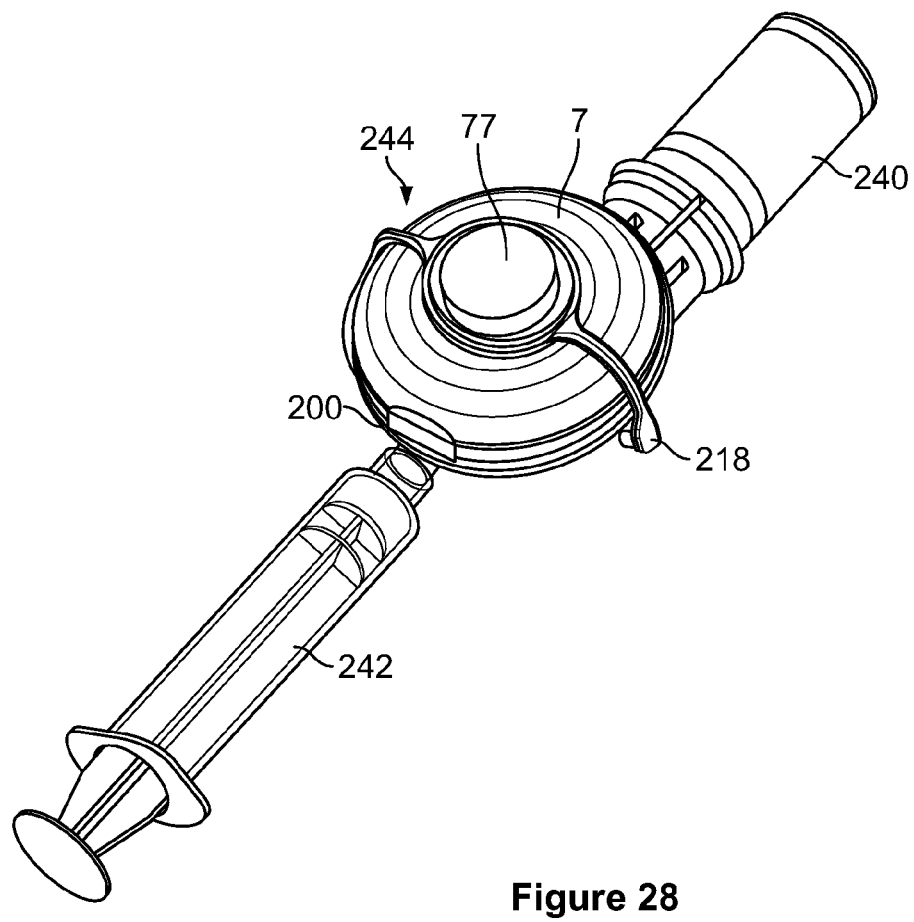
FIG. 28 is a perspective view of an injection system including an injection device generally as shown in the above FIGS. 1-20, a transfer device as in FIGS. 21-27 temporarily coupled thereto, a standard vial and a standard syringe.
Figure 29:
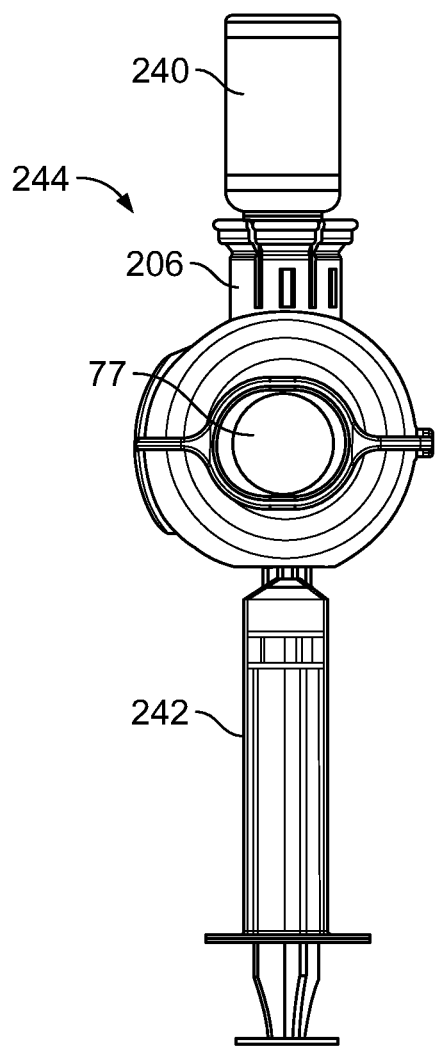
FIG. 29 is a top view of the system of FIG. 28.
Figure 30:
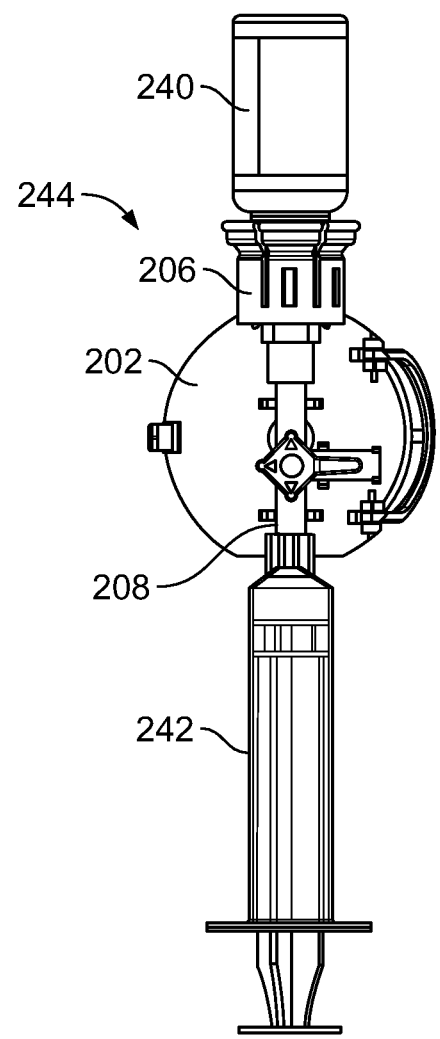
FIG. 30 is a bottom view of the system of FIG. 28.

Turning now to the transfer device and to FIGS. 21-27, the illustrated version of the transfer device 200 may include, among other features, a base 202 that includes an injection device mating or support surface 204, a vial adapter 206, a syringe adapter 208, a flow control valve 210 (see bottom view in FIG. 24), and fluid flow path segments 212, 214 and 216 (see bottom view in FIG. 24). The transfer device 200 may also include a retaining strap or harness 218 for temporarily securing the transfer device 200 to the injection device 7.

The transfer device may be made of one-piece molded plastic construction for low-volume, low cost disposability. Alternatively, one or more features of the transfer device may be separately formed and assembled together to provide the complete transfer device.

The support surface 204 may take any of a variety of configurations. The illustrated support surface is generally a circular flat surface that includes an upstanding fluid transfer port 220 positioned off-center to extend into the filling port 81 of injection device 7 when the injection device 7 is placed onto the support surface. The fluid transfer port 220 is generally in the form of a relatively small diameter hollow needle or cannula (which may have a blunt end to avoid accidental needle stick), the lower end of which is in flow communication with flow path segment 214 connected to a lower surface that is opposed to the support surface.

The base 202 may include opposed preferential gripping areas 205 (which may also be referred to as finger gaps or gripping or holding zones, regions or locations) that allow the user to grip the injection device 7 in a particular location that encourages, among other benefits, attachment of the injection device 7 to the patient in a preferred orientation. The gripping areas 205 are spaced apart around the peripheral edge of the base and may be, for example, substantially 180 degrees apart. To encourage use of the preferential gripping areas, the base may include interfering areas 207 (zones, regions or locations) located between the gripping areas 205 that are configured to interfere with or potentially prevent user gripping of the injection device 7 in those areas—thus encouraging the user to grasp or grip the injection device 7 in the intended preferential gripping areas 205. In this example, the base 202 includes preferred gripping areas 205 adjacent the support surface 204. Gripping areas 205 are defined by flat segments along the otherwise generally circular support surface 204 of the base 202. Thus, generally circular segments 207 extend between the flat segments of the gripping areas 205 and present interfering areas.

The syringe adaptor 208 is illustrated as a standard hollow female luer lock adapter with standard dimensions designed to interfit with the usual standard male syringe luer port located at the discharge end of standard syringes. The radial projections or ears 222 of the luer adapter cooperate with a threaded collar that is located around the male luer port of the standard syringe so that relative rotation secures the male and female luer portions together and avoids accidental or premature disconnection. The syringe adaptor 208 is fluidly connected to one end of fluid flow path segment 212.

The vial adaptor 206 includes an external collar 224 that is flared outwardly at the open end for guided reception of the end of a standard vial of injectable. As may be seen in FIG. 22, the vial adaptor may include one or more elongated hollow piercing spikes, pins or cannulas 226 for piercing the rubber septum that covers the end of standard medicament vials when a vial is inserted. If one cannula is used, it may include at least a fluid flow lumen for allowing liquid to enter or exit the vial and a venting lumen for allowing displacement air to enter or exit the vial. Alternatively, separate piercing pins or cannulas may be used, e.g., one cannula for liquid flow and a separate cannula for displacement air. As described later, a microporous filter, such as a hydrophobic membrane, may be provided to filter displacement air entering the vial while preventing liquid from leaking through the vent air passageway. The fluid flow lumen of the piercing pin or cannula of the vial adaptor 206 is connected to one end of fluid flow path segment 216 on the underside of the base, as will be described below.

To hold the transfer device temporarily coupled to the injection device 7, the harness 218 is pivotally attached at one side of the base 202 and can be pivoted over an associated injection device 7 to straddle the base 202 and injection device 7 and hold the injection device 7 in place. The free end 228 of the harness 218 includes a manually connectable and releasable clip or connector 230 for securing the harness over an injection device 7 and holding it against the base 202 of the transfer device 200 and for releasing the harness 218 and the injection device 7 when fluid transfer into the injection device is completed. To help avoid lateral shifting of the injection device 7 when coupled to the transfer device 200, the harness 218 has an intermediate ring 232 that extends around or circumscribes the actuator button 77 of the injection device 7.

The fluid flow arrangement of the illustrated transfer device 200 is better seen in FIG. 24. The fluid flow path segments 212, 214 and 216 may be molded as part of a one-piece transfer device 200 or may be separately formed, such as plastic tubing segments, and secured to the underside of the base 202. The actual flow path configuration can also be varied. As seen in FIG. 24, the fluid flow path segments 212, 214 and 216 communicate through a centrally located flow control valve 210 shown in the form of a 3-port valve or stopcock. More specifically, flow path segment 212 extends between the hollow female luer of syringe adapter 208 and the valve 210, the flow path segment 214 extends between the hollow cannula of the fluid transfer port 220 and the valve 210, and the flow path segment 216 extends between the hollow fluid flow piercing spike, pin or cannula 226 of the vial adapter 206 and the valve 210. The three-port valve 210 allows the user to direct/control flow between the syringe adapter 208 and the vial adapter 206 and between the syringe adapter 208 and fluid transfer port 210. Although it is feasible for the flow control valve 210 also to allow flow between the vial adapter 206 and the fluid transfer port 220, that arrangement would not typically be used in this version of the transfer device 200, and movement of the flow control valve 210 to that position may be prevented by an appropriate valve stop or the like to avoid user mishandling. To provide an indication of the valve position and the flow path segments that are in flow communication, the valve handle 236 may include visible and/or tactile indicators, such as the triangular indicators 238, seen in FIG. 24.

Filters may also be positioned in the desired fluid flow segments 212, 214 and 216 to filter the liquid injectable as it passes along the flow path, to remove air bubbles that may be entrained in the liquid and/or to allow displacement air to vent into and from a vial. These filters may be of any suitable type, although microporous membranes of average pore size such as 0.22 microns may be used for advantageous filtration. Such a filter membrane may be hydrophilic, allowing liquid to pass through, or hydrophobic, allowing gas to pass through and blocking liquid flow, or combination filters in which a portion is hydrophilic and a portion hydrophobic. The position and type of filter will depend on the objective, although one option is to employ a hydrophobic microporous filter membrane in the displacement air flow path to remove pathogens from displacement air passing therethrough while preventing liquid from passing through, and to provide a microporous hydrophilic membrane in the liquid flow path to filter any particulate or pathogens from the liquid while also removing any air bubbles entrained in the liquid. Hydrophilic microporous filters may be provided in each fluid flow path segment if desired.

The assembled system 244, including the injection device 7 and transfer device 200, is shown in FIGS. 28-40 connected to a standard injectable-containing vial 240 and a standard syringe 242. The vial and/or syringe may be attached to the transfer device 200 before or after the transfer device 200 is secured to injection device 7. This arrangement allows for user ease of withdrawal of a liquid injectable from the vial 240 into the syringe 242 and delivery from the syringe into the injection device. By positioning the handle 236 of the flow control valve 210 so that the flow path segments 212 and 216 are exclusively in communication and flow path segment 214 blocked, injectable can be drawn from the vial 240 into the syringe 242 by simply pulling back on the syringe plunger. The valve handle 236 can then be rotated so that flow path segments 212 and 214 are exclusively in communication and segment 216 is blocked. In this position, depression of the syringe plunger forces the liquid injectable from the syringe 242 into the injection device 7, causing the resilient bladder (expandable member 78) to expand as it receives the injectable, and preparing the injection device for subsequent injection into a living subject. Additional vials 240 may be attached and the contents transferred, as needed for the proper dosage. Also, if the injectable requires dilution or reconstitution, the syringe 242 may be provided prefilled with the desired amount of sterile liquid for diluting or reconstituting the injectable. Mixing or reconstitution can be enhanced, if desired, by leaving the valve 210 in the position where the vial 240 and syringe 242 are in communication, and repeatedly cycling the syringe plunger to force liquid back and forth between the vial 240 and syringe 242.

Additional features or aspects of this particular embodiment may be recognized in that a hand-held syringe transfer system is provided to allow for a compact and efficient way to remove drug from a vial and move it into a syringe and then into an injection device.

During basic operation, the user attaches the vial of drug to the system assembly 244 with the vial adapter 206 of the transfer device 200. The drug vial 240 can have a capacity of 1-50 mL with neck finishes of 13-20 mm. The syringe 242 capacity can be 1-50 mL. The injection device 7 capacity can be 1-50 mL. The user can attach the drug vial to the vial adapter and then attach it to the system. Alternatively, the vial adapter would be part of the system and the user inserts the vial 240 into the system. The vial adapter 240 may contain a spike 226 to access the drug vial 240 through the rubber stopper and has two fluid paths. One vented to atmosphere and the other connected to the fluid path. This allows for easy withdraw of the fluid from the vial 240 without creating a vacuum. The syringe 242 is connected to the other side for withdraw of the fluid from the vial 240 and transfer of the fluid into the injection device 7. Once the vial 240 and syringe 242 are attached to the system 244, the valve is positioned to withdraw state creating a fluid path between the syringe 242 and the vial 240. By pulling on the syringe plunger, fluid is withdrawn from the vial 240 into the syringe 240. The entire contents of the vial 240 can be removed or partial contents based on the patient's dose. The user can attach multiple vials 240 to fill one syringe 242 to get a necessary dose into the syringe 242. If the fluid is hard to push out of the syringe 242, the user can use multiple syringes 242 to go into the injection device 7 from one or more vials 240. Prior to determining the final dose, there may be some air in the syringe 242. The user can prime the syringe 242 by expelling the excess air in the syringe 242 back into the vial 240.

Once the desired amount of fluid is removed from the vial 240 and into the syringe 242, the valve 210 is switched to fill. This creates a fluid path between the filled syringe 242 and the injection device 7. The user pushes on the plunger of the syringe 242 to expel the contents of the syringe 242 into the injection device 7. If air exists in the syringe 242 during transfer, the system 244 can filter air to prevent air from being transferred into the injection device 7. A filter in the fluid path between the syringe 242 and the injection device 7 can filter the air. This can be accomplished with a hydrophobic filter or combination of hydrophilic/hydrophobic filter, as above discussed. The retaining strap or harness 218 can be unlocked and the filled syringe 242 can be removed from the system 244. Alternatively, the drug may come in a prefilled syringe 242. Thus, the valve handle 236 would be moved to the transfer position and the drug pushed into the injection device 7. Multiple prefilled syringes 242 could be used to fill the injection device 7. When filling of the injection device 7 is complete, the transfer device 200 may be readily removed and discarded with little waste, and the injection device 7 applied to the patient.

Figure 31:
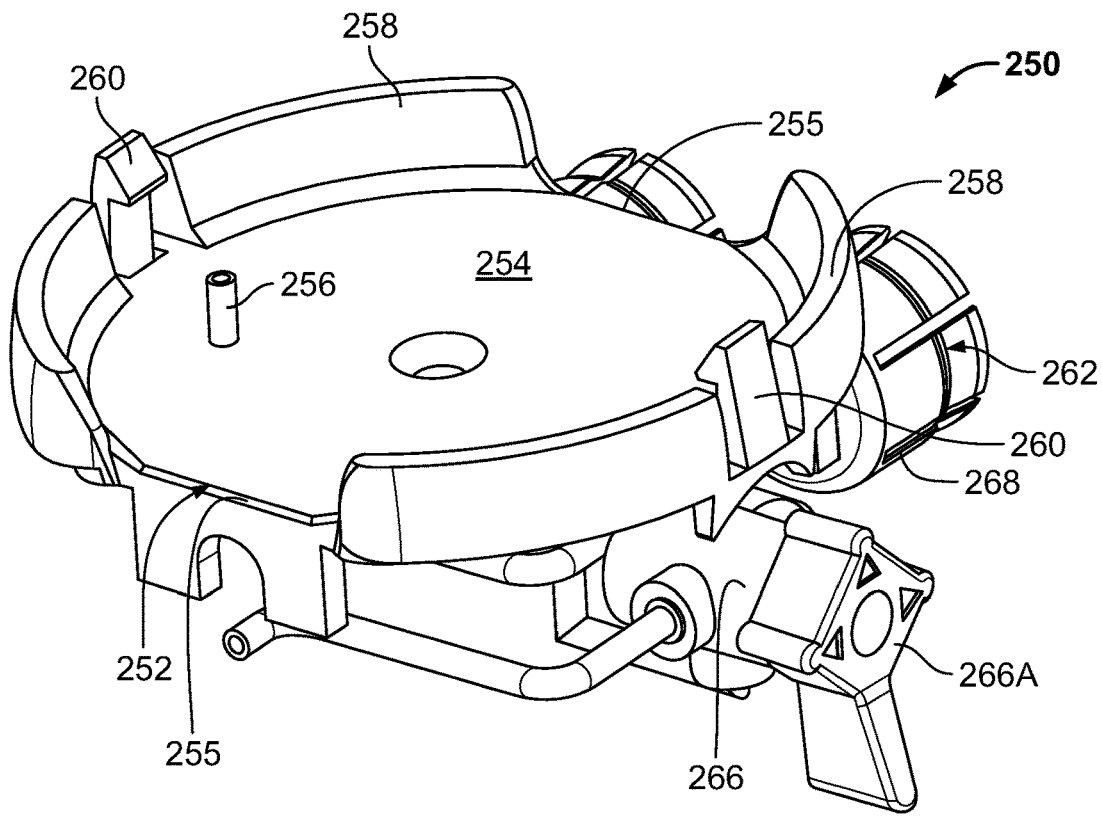
FIG. 31 is a perspective view of a transfer device for temporary coupling to an injection device such as the device shown in the figures above for manipulating/transferring an injectable from a plurality of vials into the injection device.

FIGS. 31-44 relate to another embodiment of a transfer device 250 particularly suited for injectables that require reconstitution or dilution. This transfer device 250 includes some characteristics similar to those of the transfer device 200 shown in FIGS. 21-30, but includes two vial adapters 262 and a necessarily different flow path arrangement. As seen in FIG. 31, this transfer device 250 includes a base 252 upon which the injection device 7 rests when coupled thereto. The base 252 forms a support surface 254 from which a fluid transfer port 256 projects for insertion into the filling port 81 of the injection device 7. Raised peripheral walls 258 extend upwardly from the support surface 254, and together they define a nesting or docking site for receiving the injection device 7. The injection device 7 may be temporarily held in the coupled position on the transfer device 250 by opposed flexible hooks 260 that flex outwardly to receive the injection device 7 and hook over the peripheral edge of the disc-shaped injection device 7 to removably retain it on the transfer device 250. Alternatively or additionally, a harness arrangement as described earlier may be used for temporarily coupling the transfer device 250 to the injection device 7. Likewise, the retaining hooks 260 of this embodiment may also be used in the prior single-vial embodiment.

As in the previous example, the base 252 of this example may include opposed preferential gripping areas 255, which may be referred to as finger gaps or gripping or holding zones, regions or locations and that similarly allow the user to grip the injection device 7 in a particular location that encourages, among other benefits, attachment of the injection device 7 to the patient in a preferred orientation. The gripping areas 255 are spaced apart around the peripheral edge of the base 252 and may be, for example, substantially 180 degrees apart. To encourage use of the preferential gripping areas 255, the base may include interfering areas (zones, regions or locations) located between the gripping areas 255. In this example, the gripping areas 255 are defined by flat segments along the otherwise generally circular support surface 254 of the base 252, and the interfering areas are adjacent the support surface 254 and defined by the upward extending raised peripheral walls 258. Thus, the peripheral walls 258 extending between the flat segments 255 provide interfering areas that are configured to interfere with or potentially prevent user gripping of the injection device 7 in those areas, so as to encourage the user to grasp or grip the injection device 7 in the intended preferential gripping areas 255.

Figure 32:
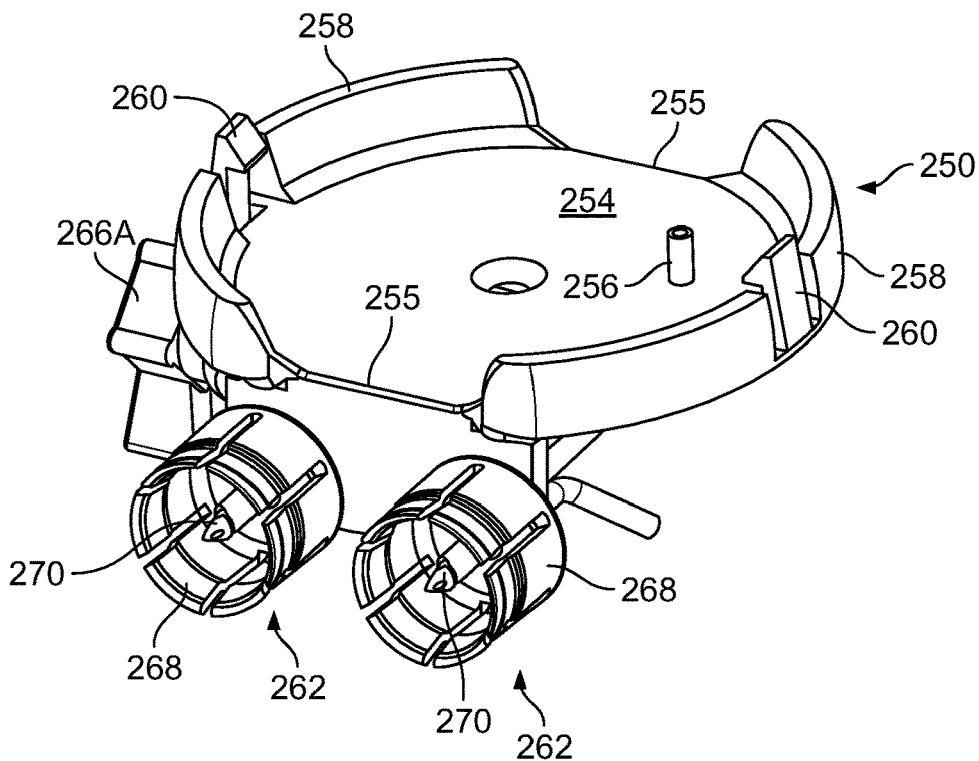
FIG. 32 is a perspective view of a transfer device of FIG. 31, taken from a different angle.
Figure 33:
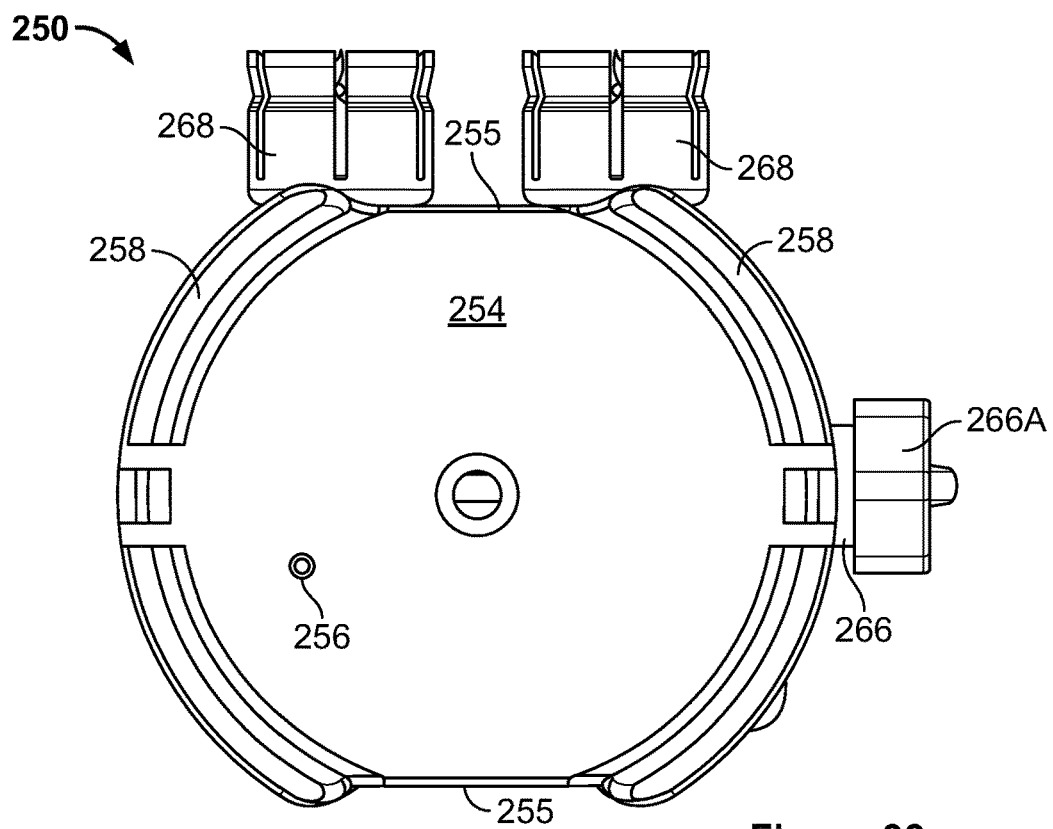
FIG. 33 is a top view of the transfer device of FIG. 31.
Figure 38:
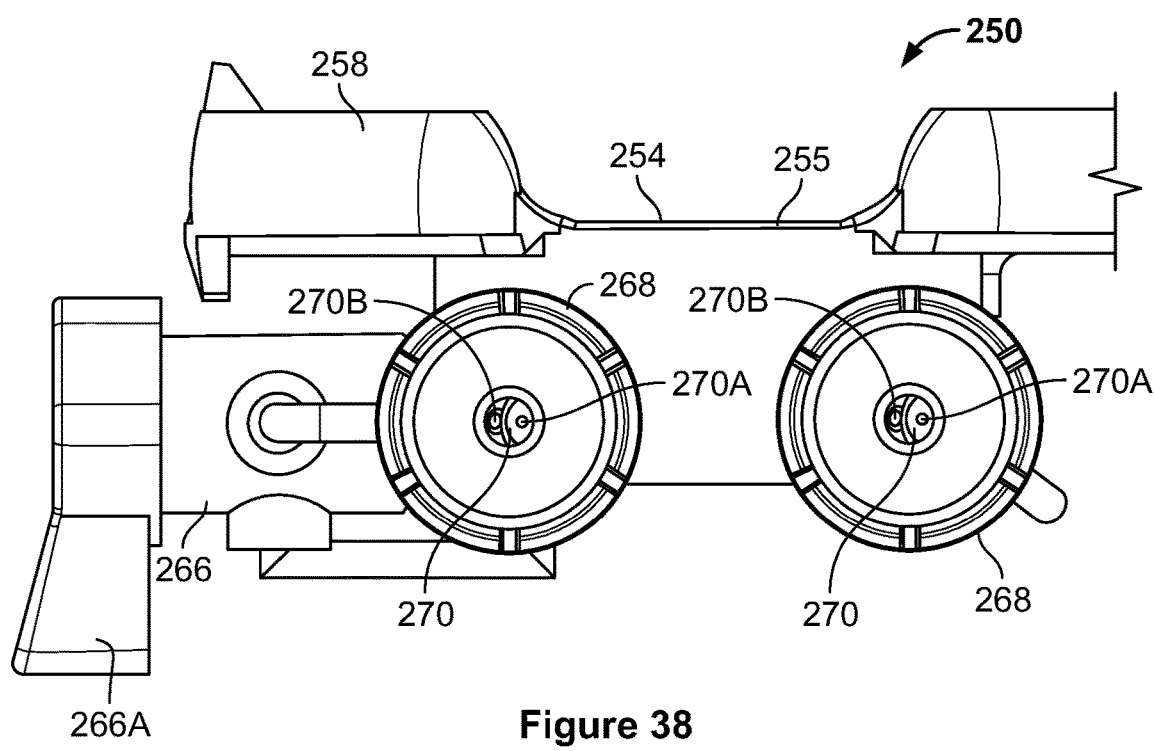
FIG. 38 is an end view of the transfer device of FIG. 31 looking directly at a pair of vial adapters.

As noted earlier, the transfer device 250 includes a pair of vial adapters 262 (262A, 262B), a syringe adapter 264, a fluid flow control valve 266 having a valve handle 266A and associated flow path segments, better seen in other figures. Referring to FIG. 32, each vial adapter 262 is similar to that described above in the single-vial embodiment, with an external collar 268 and a hollow piercing pin or cannula 270 for piercing the septum that seals the open end of a standard medicine vial. As described earlier in connection with the prior embodiment, each vial adapter 262 may include a venting feature that allows displacement air to enter or leave the vials and such a venting feature may, for example, be provided as an additional lumen in the piercing pin 270 or as an additional hollow piercing pin or cannula that is devoted to movement of venting air to and from the vial and vented to the atmosphere. FIG. 38, which is a view into the vial adapters 262 shows piercing spikes, each with two lumen 270A, 270B—one for liquid introduction and withdrawal and one for venting.

Figure 34:
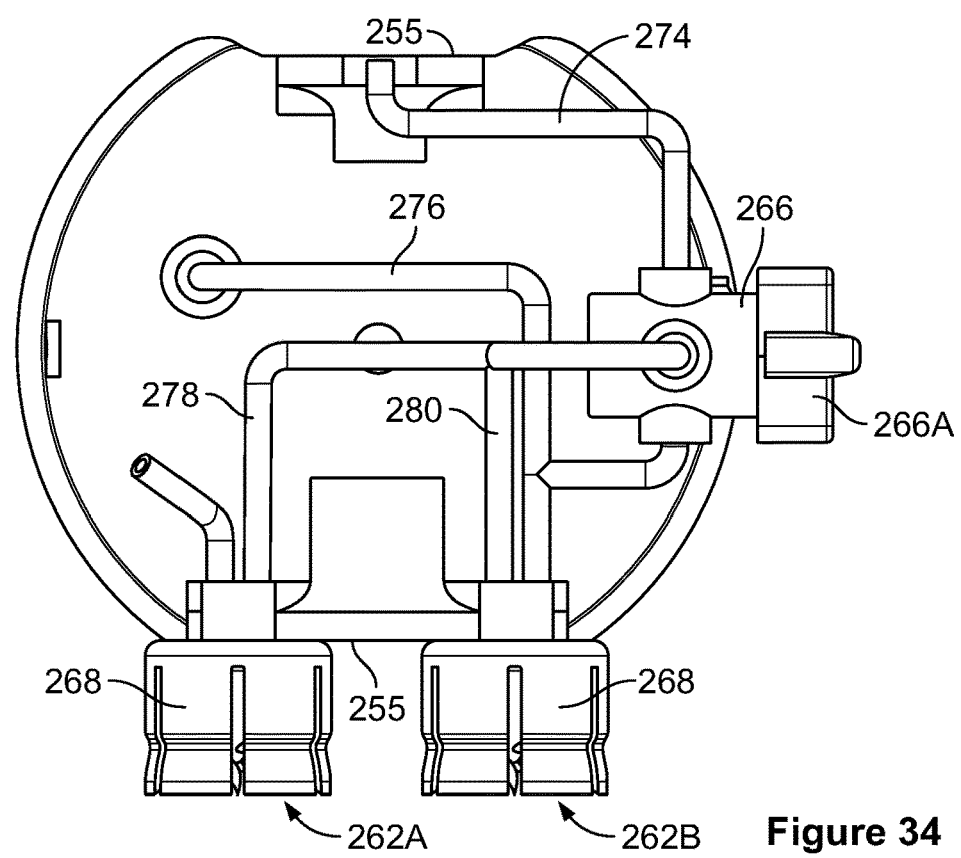
FIG. 34 is a bottom view of the transfer device of FIG. 31.
Figure 35:
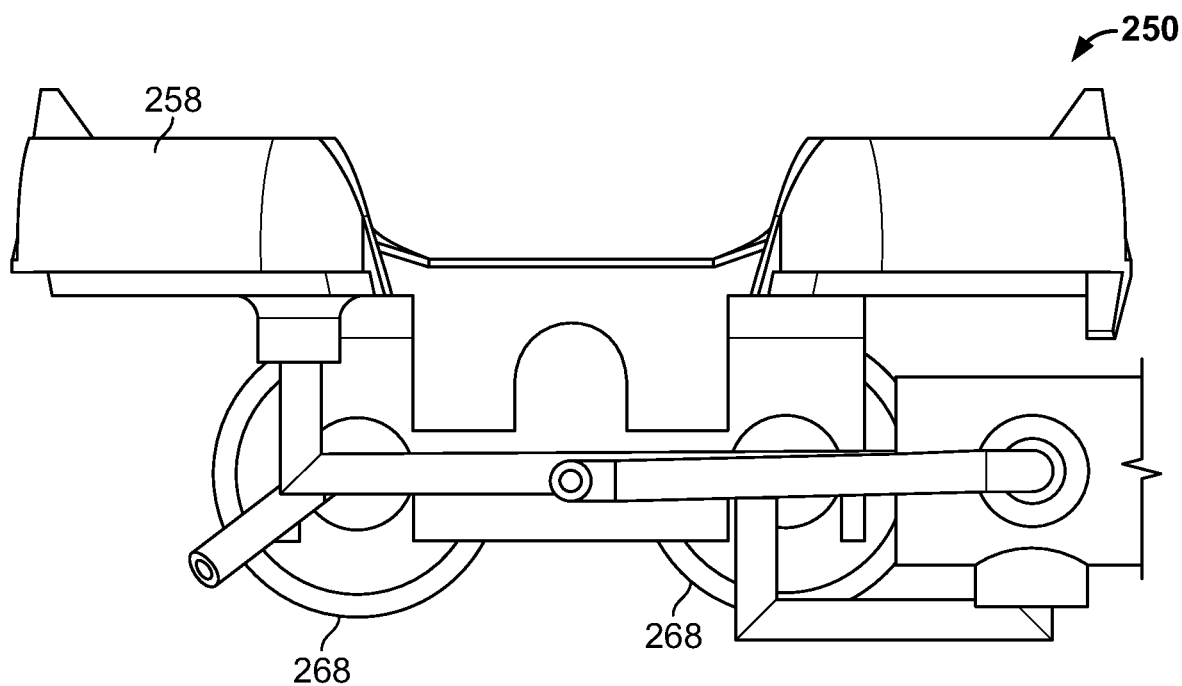
FIG. 35 is an end view of the transfer device of FIG. 31 looking directly at a syringe adapter, with portions removed.
Figure 36:
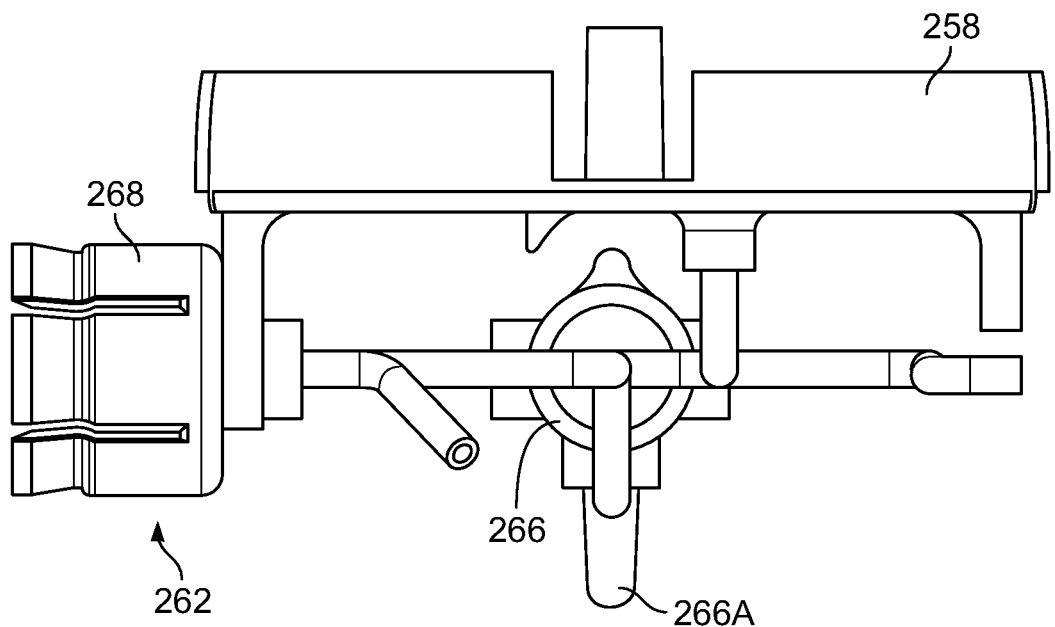
FIG. 36 is a side view of the transfer device of FIG. 31.
Figure 37:
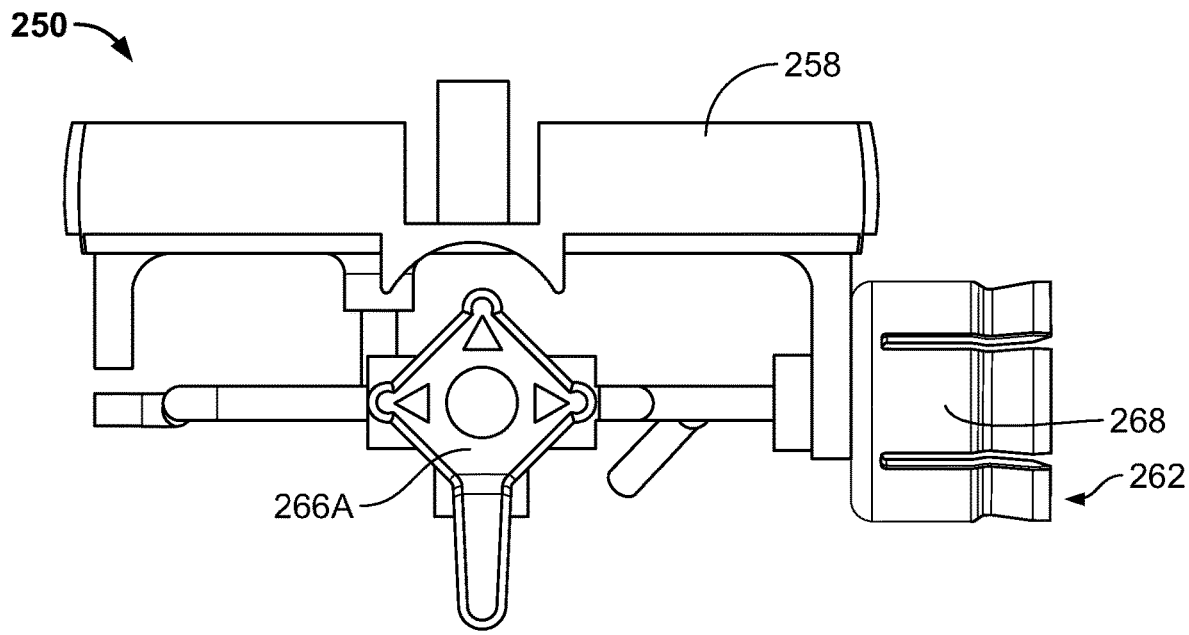
FIG. 37 is an opposite side view of the transfer device of FIG. 31.

One example of a fluid flow path arrangement for this transfer device 250 is seen in FIG. 34, which is a view of the underside of the transfer device 250. As shown, a fluid flow path segment 274, such as a length of plastic tubing, extends between flow control valve 266 and syringe adapter 264. Fluid flow path segment 276 extends between the flow control valve 266 and the fluid transfer port 256. Fluid flow path segment 278 extends between the flow control valve 266 and the diluent vial adapter 262A, and fluid flow path segment 280 extends between the flow control valve 266 and the injectable vial adapter 262B.

The fluid flow arrangement here allows the ready use of the transfer device 250 when the injectable requires reconstitution or dilution. The injectable vial may be attached to one of the vial adapters 262B and the diluent used to reconstitute or dilute attached to the other vial adapter 262A. After the diluent and injectable vials 240A, 240B and the syringe 242 are attached to the transfer device 250, the valve handle 266A of the flow control valve 266 is positioned to allow flow between the diluent vial adapter 262A and the syringe 242. Retracting the syringe plunger draws diluent from the diluent vial 240A into the syringe 242. The valve handle 266A of the flow control valve 266 is then repositioned to place the syringe 242 and the injectable vial 240B into flow communication and the diluent is injected into the injectable vial 240B to reconstitute the injectable. As described earlier, reconstitution may be promoted by manually shaking the entire assembly and/or by cycling the syringe plunger back and forth to repeatedly withdraw fluid from and inject fluid into the injectable vial 240B, causing agitation and mixing of the diluent and injectable. The reconstituted injectable is then collected into the syringe 242. These steps may be carried out before or after coupling of transfer device 250 to the injection device 7, and may be repeated with additional diluent and injectable vials 240A, 240B, if necessary for increased dosage. If carried out prior to attachment of the injection device 7, the injection device 7 will then be coupled to the transfer device 250 and the valve 266 repositioned again to place the syringe 242 (which contains the reconstituted injectable) and fluid transfer port 256 into fluid communication, and depression of the syringe plunger forces the reconstituted injectable through the fluid transfer port 256 and the filling port 81 into the injection device 7, expanding the resilient expandable member or bladder 78 and preparing the injection device for use.

Figure 39:
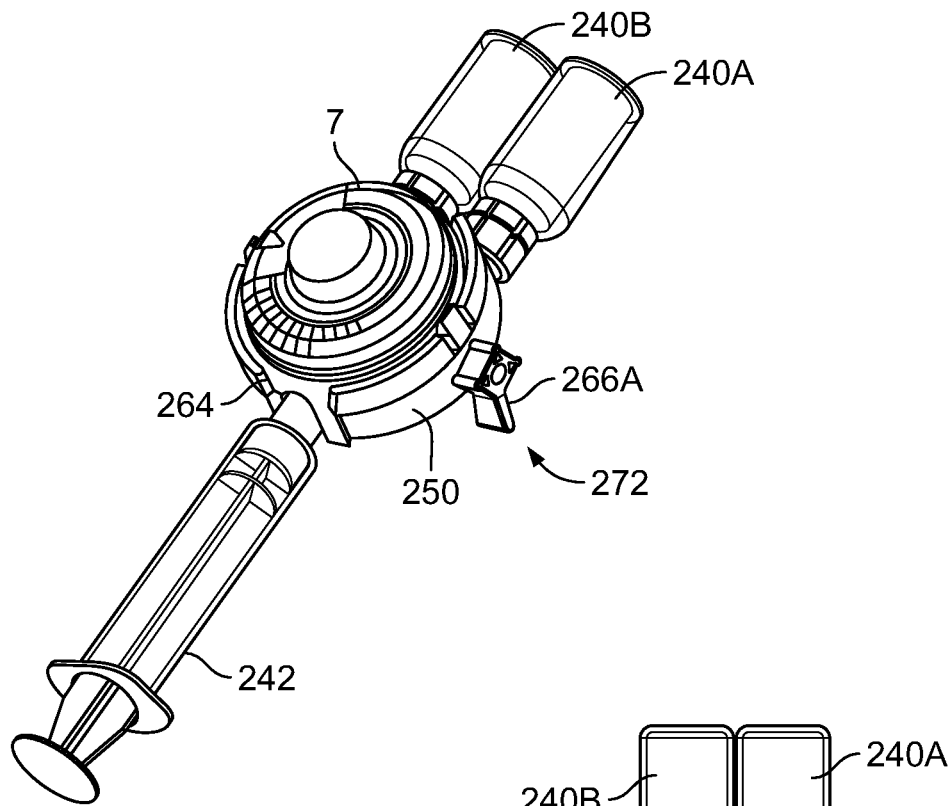
FIG. 39 is a perspective view of an injection system including an injection device generally as shown in the above FIGS. 1-20, a transfer device as in FIGS. 31-38 temporarily coupled thereto, a pair of standard vials and a standard syringe.
Figure 40:
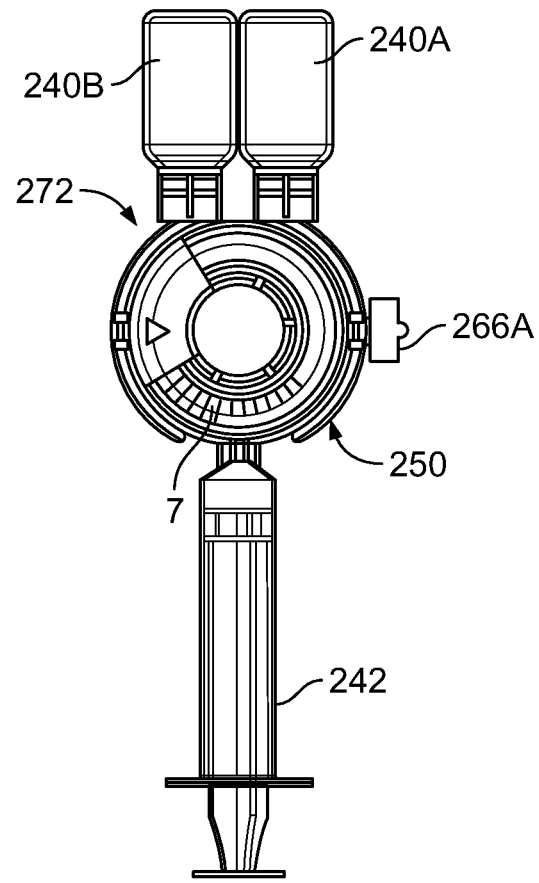
FIG. 40 is a top view of the system of FIG. 39.
Figure 41:
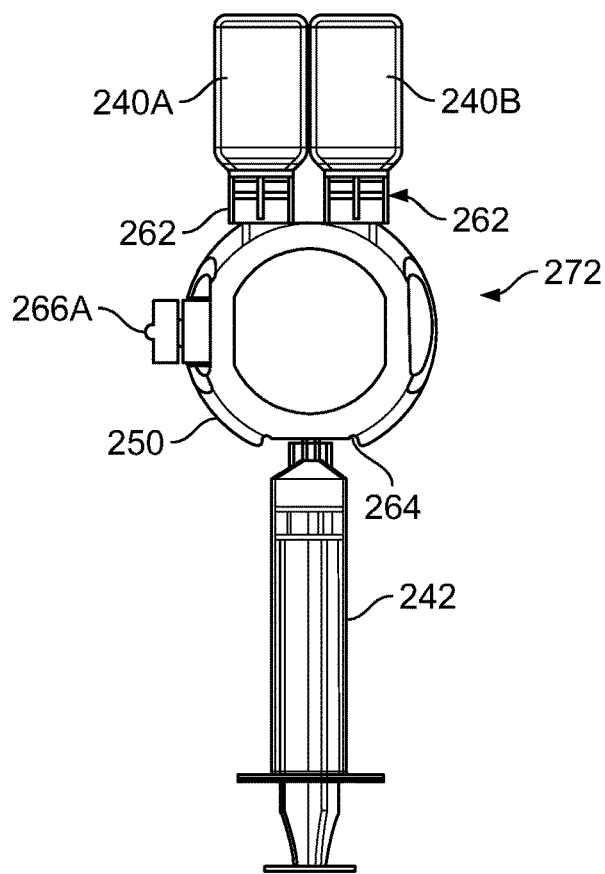
FIG. 41 is a bottom view of the system of FIG. 39.

The assembled two-vial system 272, including the injection device 7 and transfer device 250, is shown in FIGS. 39-41 connected to a standard injectable-containing vial 240B, standard diluent containing vial 240A and a standard syringe 242. The vials 240A, 240B and/or syringe 242 may be attached to the transfer device 250 before or after the transfer device 250 is secured to the injection device 7. This arrangement allows for user ease of reconstitution or dilution of the injectable and delivery into the injection device 7.

Additional features or aspects may also be recognized in that a hand-held reconstitution syringe transfer system is provided to allow for a compact and efficient way reconstitute lyophilized drug, remove drug from a vial and move it into a syringe and then into an injection device. During basic operation, the user attaches the lyophilized drug and diluent vials to the system assembly 272 with the vial adapter(s). Each drug and diluent vial can have a capacity of 1-50 mL with neck finishes of 13-20 mm. The syringe 242 capacity can be 1-50 mL. The injection device 7 capacity can be 1-50 mL. The user can attach the lyophilized drug and diluent vial(s) to the vial adapter 262, then attach it to the system 272. Alternatively, the vial adapter would be part of the system 272 and the user inserts the vial(s) into the system 272. The vial adapter(s) 262 contain a spike 279 to access the vial through the rubber stopper and has two fluid paths. A first vial adapter with one vented to atmosphere and the other connected to the fluid path. This allows for easy withdraw of the fluid from the vial without creating a vacuum. The other vial spike would allow for connection of two independent sources. The syringe 242 is connected to the other side for withdraw of the fluid from each of the diluent vial 240A and/or reconstituted vial 240B and transfer of the fluid into the injection device 7. Once the vial(s) and syringe are attached to the system, the valve 266 is positioned to State 1 creating a fluid path between the diluent vial 240A and syringe 242 and allowing withdraw of the diluent into the syringe 242. By pulling on the syringe plunger, fluid is withdrawn from the diluent vial 240A into the syringe 242. The entire contents of the diluent vial 240A can be removed or partial contents based on the patient's dose. The user can attach multiple diluent vials to fill one syringe 242 to get a necessary dose into the syringe 242. The user then can switch the valve to State 2. This creates a fluid path from the filled syringe 242 (with diluent) to the lyophilized vial 240B.

In an alternative embodiment, the diluent comes in a prefilled syringe. In this case, the diluent can be directly transferred to the lyophilized vial. (This can also be accomplished in the single vial system). The user can push on the plunger of the syringe to transfer the contents of the syringe to the lyophilized vial.

In a further alternative embodiment, the lyophilized vial may be under vacuum. By insertion of the diluent vial and lyophilized vial, the vacuum in the lyophilized vial automatically pulls the diluent into the lyophilized vial. Once the diluent is transferred to the lyophilized vial, the reconstitution process can begin. The user can manually agitate the diluent/powder mixture until the powder is completely dissolved in solution. The user can then pull back on the syringe plunger to pull the entire contents of the mixed solution or a partial dose, depending on what was prescribed. Prior to determining the final dose, there may be some air in the syringe 242. The user can prime the syringe by expelling the excess air in the syringe back into the vial. Once the desired amount of fluid is removed from the vial and into the syringe, the valve is switched to State 3. This creates a fluid path between the filled syringe 242 and the injection device 7. The user pushes on the plunger of the syringe 242 to expel the contents of the syringe into the injection device 7. If air exists in the syringe 242 during transfer, the system can filter air to prevent air from being transferred into the injection device 7. A filter in the fluid path between the syringe 242 and the injection device can filter the air. This can be accomplished with a hydrophobic filter or combination of hydrophilic/hydrophobic filter. The retaining strap, if used, can be unlocked and the filled syringe can be removed from the system.

Figure 42:
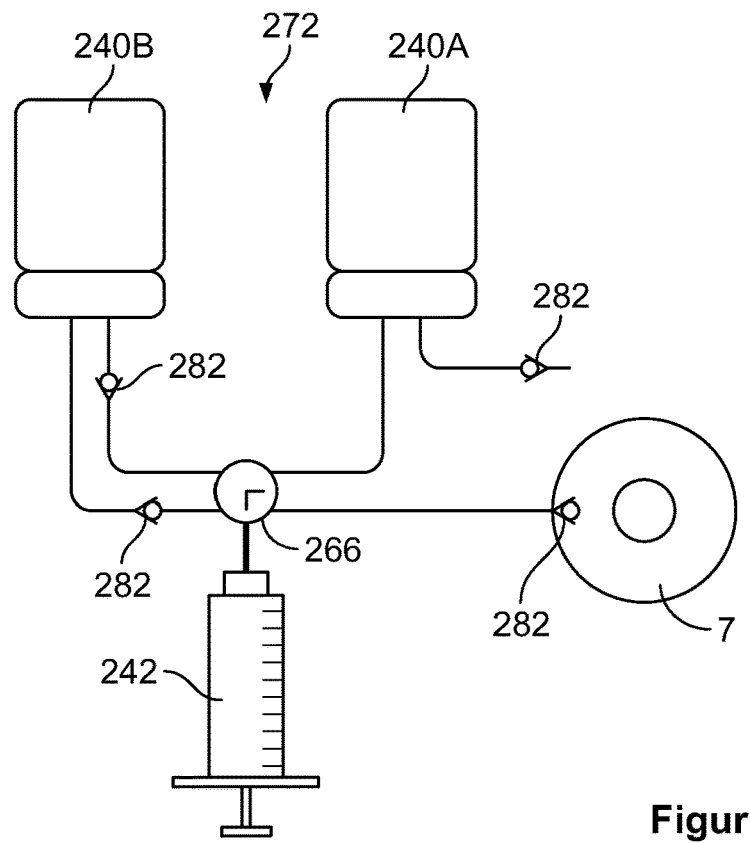
FIG. 42 is a schematic of the flow arrangement of the system of FIG. 39 in a first valve position.
Figure 43:
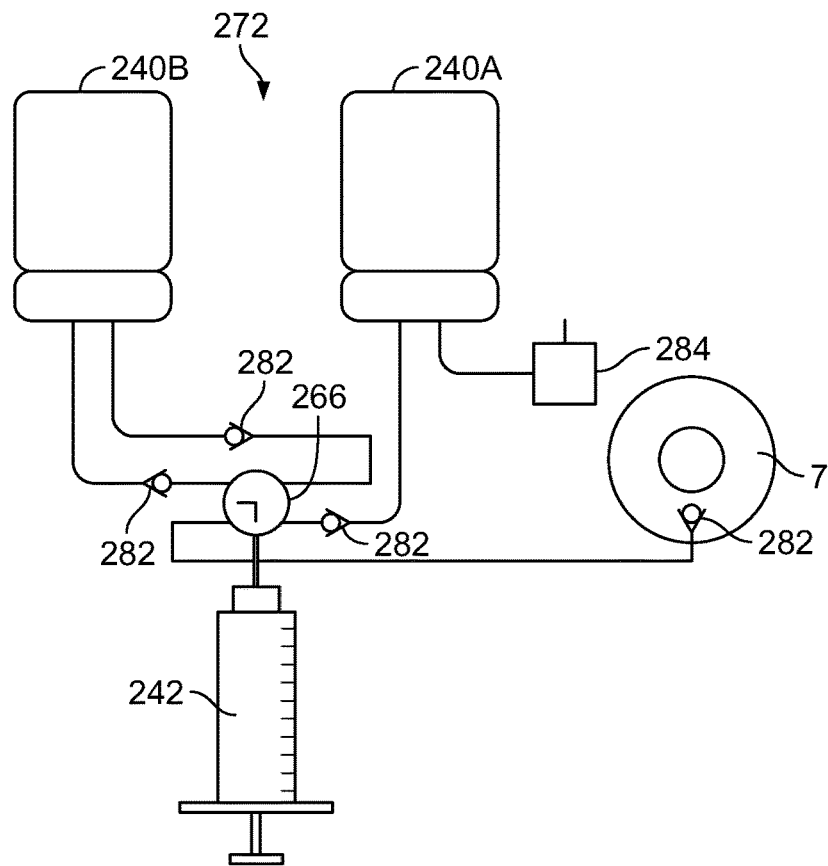
FIG. 43 is a schematic of the flow arrangement of the system of FIG. 39 in a second valve position.
Figure 44:
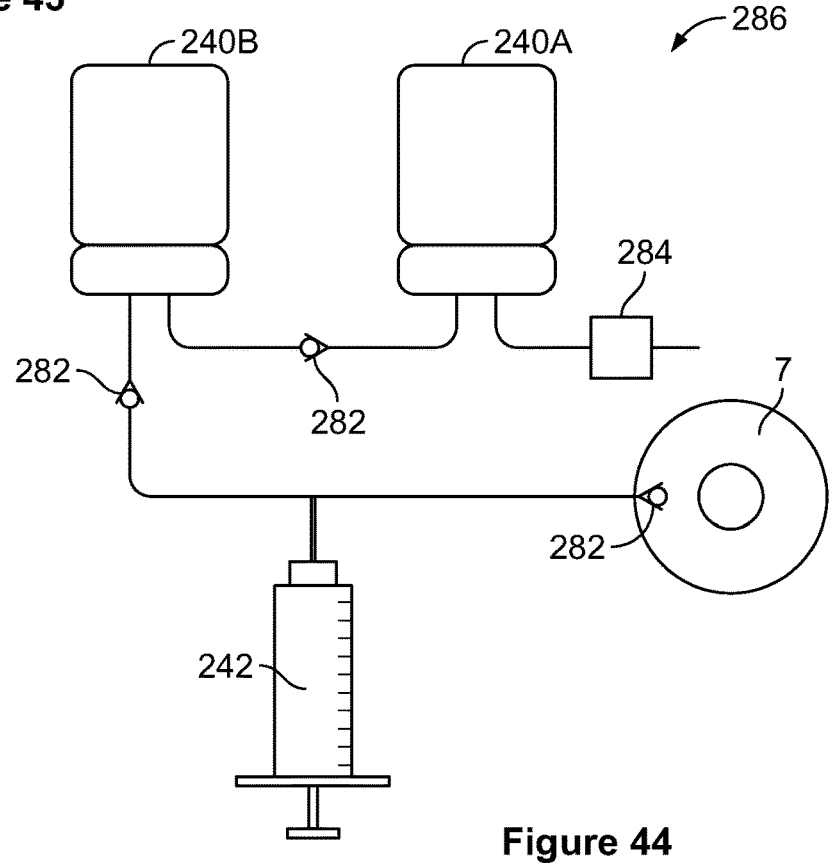
FIG. 44 is a schematic of an alternative flow arrangement of the system of FIG. 39.

FIGS. 42 and 43 are schematic flow diagrams that show a dual vial system 272 including an injection device 7 (OBDD) and three way valve 266 or stopcock, connected to a syringe 242, diluent vial (D) 240A and injectable vial (P) 240B, which system also employs check valves 282 that limit flow to one direction only and an air vent 284. FIG. 42 shows the valve position for drawing diluent from the diluent vial 240A into the syringe 242 and FIG. 43 shows the valve position after diluent has been drawn into the syringe 242 for injecting the diluent from the syringe 242 into the injectable vial 240B. FIG. 44, also a flow schematic, shows a dual vial system 286 but without a central valve or stopcock and instead relying on one-way valves 282 only to control flow. In this system 286, vacuum created by pulling back on the syringe plunger draws diluent from the diluent vial 240A through the injectable vial 240B and into the syringe 242. This system 286 may find particular application for injectables that require dilution only or for injectables that readily reconstitute in the presence of diluent. The one-way valves 282 only allow fluid flow in one direction through the system—from the diluent vial 240A to the injectable vial 240B, from the injectable vial 240B to the syringe 242, and from the syringe 242 into the injection device 7 (OBDD).

Figure 45:
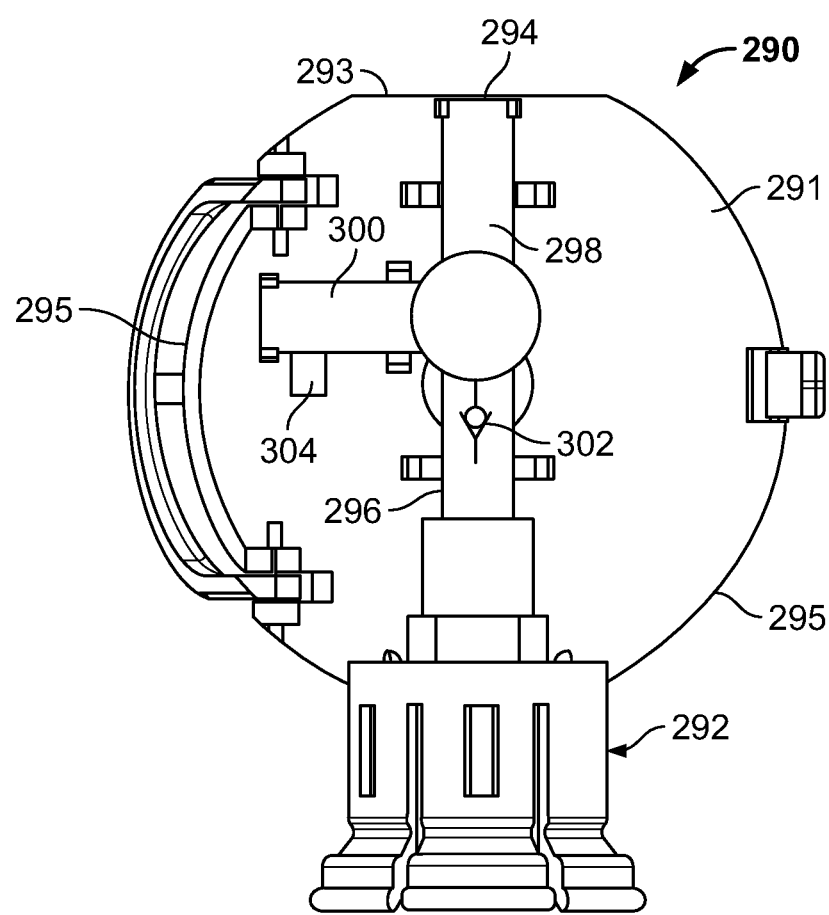
FIG. 45 is a bottom view of an alternative one vial transfer device like that shown in FIGS. 21-24, but which does not employ a movable valve, and shows an optional hydrophobic filter.

FIG. 45 is a bottom view of a transfer device 290 configured to receive one-vial, like the device 200 shown in FIGS. 21-24, but which does not use a movable valve. Thus, FIG. 45 shows a base 291 having lower surface that is opposed to a support surface (not shown in this figure) that is configured to receive an injection device 7. The transfer device 290 includes preferential gripping areas 293 and interfering areas 295, which are located and defined in a similar manner to the gripping areas 205 and interfering areas 207 of the first example transfer device 200.

This transfer device 290 also has a vial adapter 292 and a syringe adapter 294 and a fluid flow path with three branches 296, 298 and 300 that are connected to the lower surface of the base 291 and communicate respectively with the vial adapter 292, the syringe adapter 294 and the fluid transfer port (not shown in this figure). Branch 296 includes a one-way or check valve 302 that only allows flow through the branch in a direction from the vial adapter 292. This permits a syringe connected to the syringe adapter 294 to withdraw injectable from a vial attached to the vial adapter 292 and to inject it through the fluid transfer port into an associated injection device without a user having to move any valve. This device 290 may also include an optional hydrophobic filter 304 in communication with branch 300 and the ambient environment. This filter 304 allows any air preceding the injectable ("front end air") to exit or vent to the ambient atmosphere so that such air will not be forced into the injection device. The hydrophobic filter membrane prevents injectable from passing through the vent passageway so that all of the injectable is flowed into the injection device. Such a filter 304 may also be used in flow path segment 276 in the dual vial transfer device.

Additiona+l Embodiment

FIGS. 46-52 illustrate another embodiment of a hand-held transfer device 400 and system 401. The original element numbers for the injection device 7, vial 240 and syringe 242 will be retained, and new element numbers will be used for the other features of this embodiment.

Figure 46A:
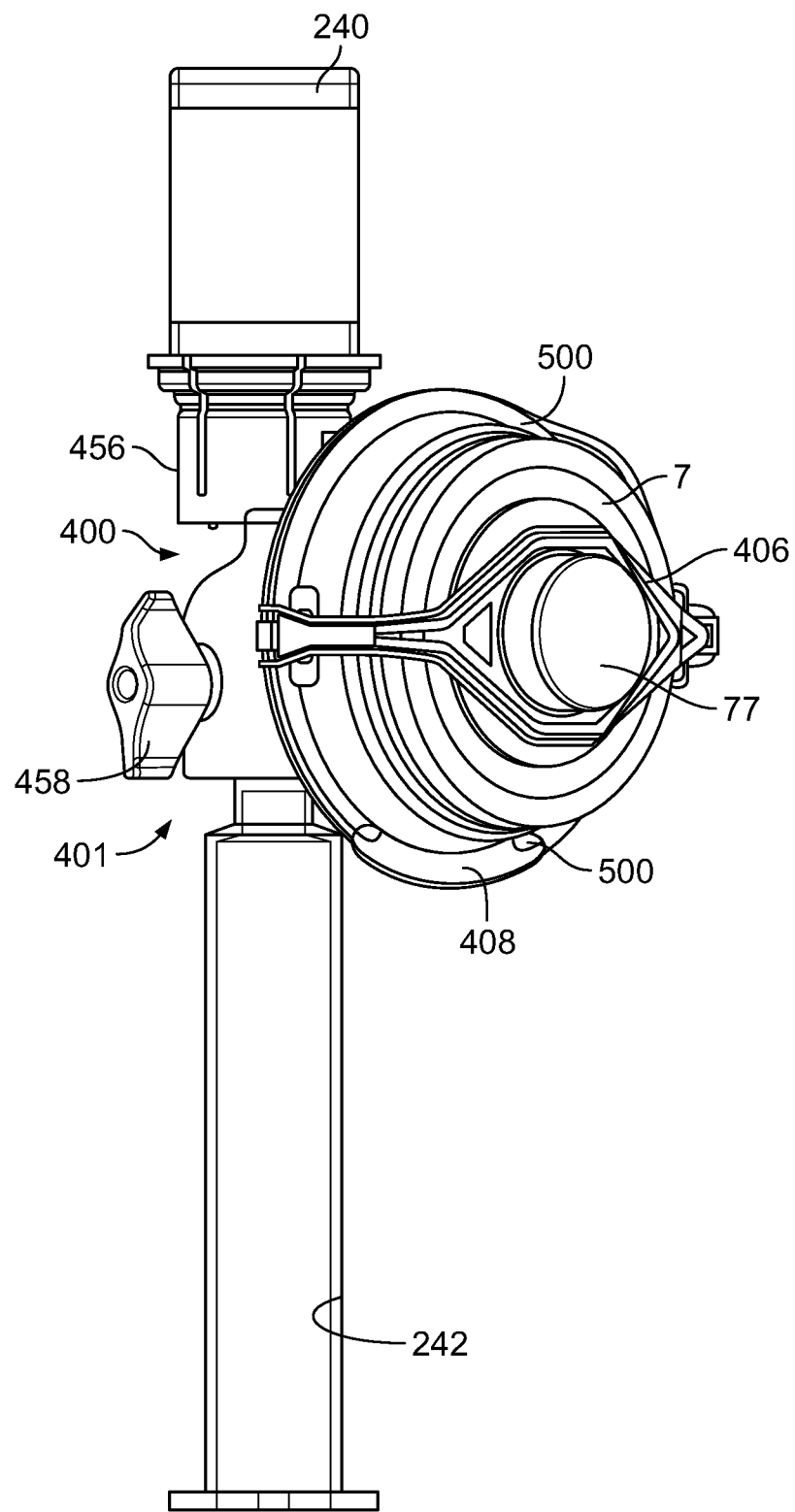
FIGS. 46a and 46b show another embodiment of the transfer device and system that is shown above, the differences being essentially in the transfer device and not in injection device 7.
Figure 46B:
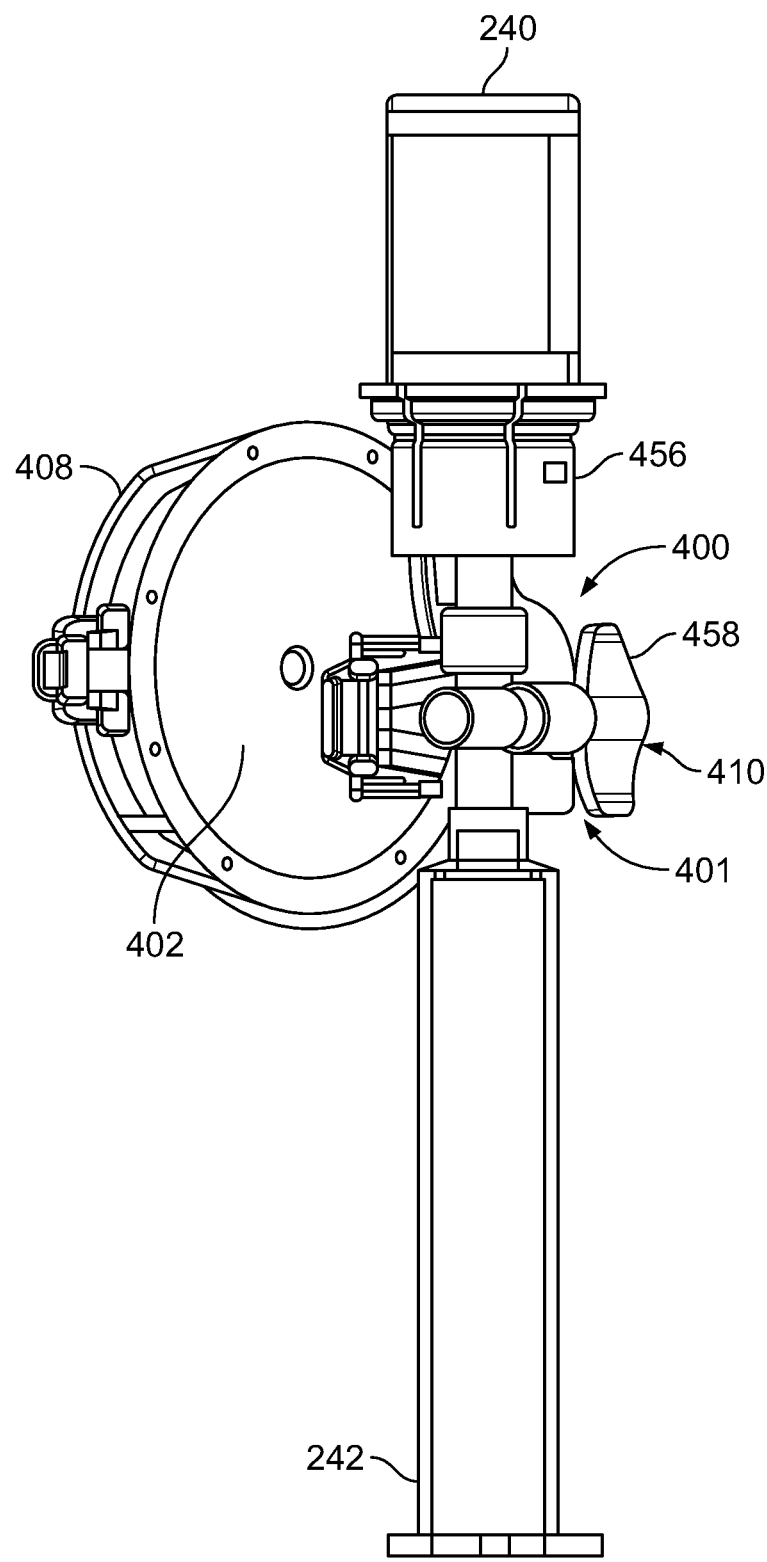
Figure 47:
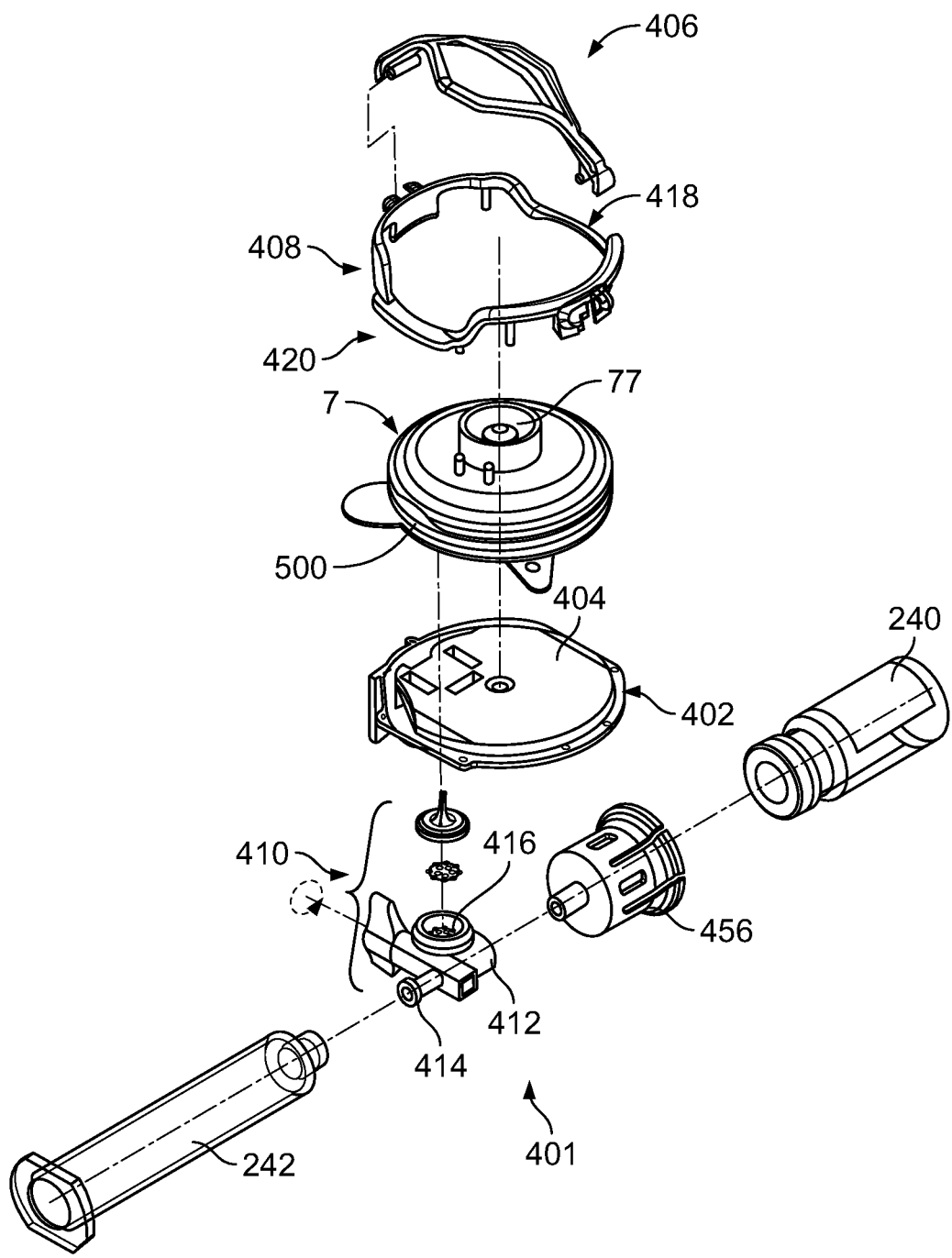
FIG. 47 is an exploded perspective view of the transfer device and system shown in FIG. 46.

Turning to FIGS. 46a, 46b and 47, these figures depict an assembled transfer system 401 comprising the injection device 7 mounted on a modified transfer device 400, with a vial 240 and syringe 242 attached to the transfer device 400. FIGS. 46a and 46b are taken from different viewing angles, allowing the assembly to be viewed from opposite sides of transfer device 400. As labeled in the figures, the illustrated transfer device 400 includes base 402 one side of which forms a support surface 404 shown in FIG. 47, against which the injection device 7 rests, as seen in FIG. 46a. A harness or retainer 406 holds the injection device 7 on the transfer device base 402 within a peripheral locator ring or ring structure 408 that is attached to the base 402. A valve 410, such as a three-way stopcock valve assembly, is mounted on the underside of the base 402 and provides selective fluid communication among the injection vial 240, syringe 242 and injection device 7 when they are, respectively, secured to the valve subassembly 410, vial port 412, syringe port 414 and upstanding injection device fluid transfer port 416 (see FIGS. 47, 51a and 51b) associated with the valve subassembly 410. The basic operating principles for fluid transfer in this embodiment are essentially the same as previously described, and the following description will focus on certain structural differences as compare to the prior embodiments.

The transfer device 400 in this embodiment has particularly helpful ergonomic features that provide a user physical interface which encourages proper user handling and placement of the injection device 7 during the various steps associated with an injection of medicament into a patient/user. In one embodiment, the transfer device 400 may include opposed preferential gripping areas (which may also be referred to as finger gaps or gripping or holding zones, regions or locations) that allow the user to grip the injection device in a particular location that encourages, among other benefits, attachment of the injection device 7 to the patient in a preferred orientation. The gripping areas are spaced apart around the peripheral edge of the base and may be, for example, substantially 180 degrees apart. To encourage use of the preferential gripping areas, the base may include interfering areas (zones, regions or locations) located between the gripping areas that are configured to interfere with or potentially prevent user gripping of the injection device in those areas—thus encouraging the user to grasp or grip the injection device 7 in the intended preferential gripping areas.

Referring to FIG. 47, one side of the base 402 in this embodiment (which may be referred to as the top side or upper side for convenience only) provides the planar support surface 404 upon which the injection device 7 rests when secured to the base 402. The base 402 of this example may include opposed preferential gripping areas 403, which similarly may be referred to as finger gaps or gripping or holding zones, regions or locations, and that allow the user to grip the injection device 7 in a particular location that may encourage, among other benefits, attachment of the injection device 7 to the patient in a preferred orientation. The gripping areas 403 are spaced apart around the peripheral edge of the base 402 and may be, for example, substantially 180 degrees apart. In this example, the gripping areas 403 are defined by flat segments along the otherwise generally circular support surface 404 of the base 402. Thus, generally circular segments 405 extend between the flat segments of the gripping areas 403 and present interfering areas that are configured to interfere with or potentially prevent user gripping of the injection device 7 in those areas, so as to encourage the user to grasp or grip the injection device 7 in the intended preferential gripping areas 403.

Figure 53M:
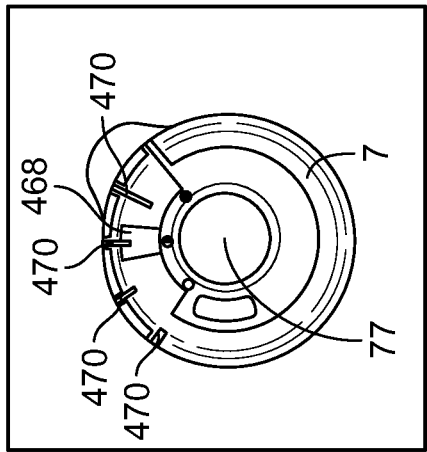
FIGS. 53A-53O are pictorial flow charts illustrating selected steps in the use of the transfer device and system.
Figure 53L:
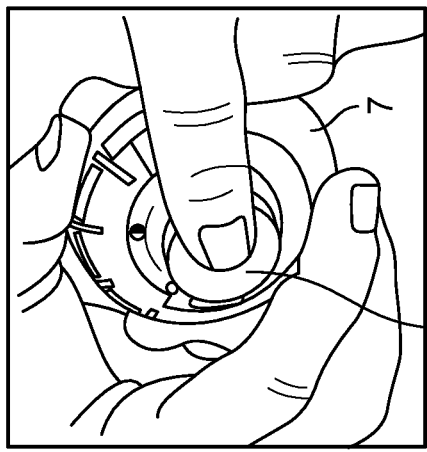
Figure 53K:
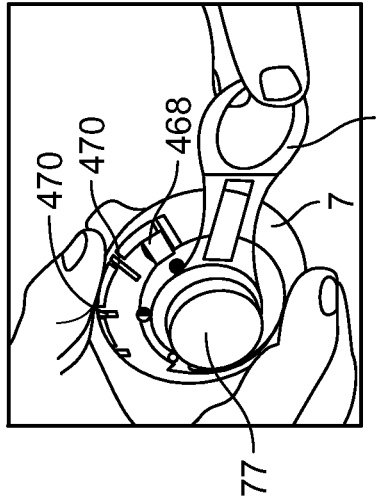

In the illustrated embodiment, the preferential gripping areas are further defined in part by the locator ring or ring structure 408 that is attached to the base 402. The locator ring 408 is shown as a separate piece (but may be optionally molded as a single piece with the base), and is located on the upper surface of the base, at least partially surrounding the support surface 404. The ergonomic configuration that encourages proper user grasping and placement of the injection device 7 is shown, for example, in FIGS. 47 and 49a and 49b. The illustrated locator ring 408 defines preferred gripping or holding areas, regions or locations 418 and 420 that force or at least encourage a user to grasp the injection device 7 at those locations and that, in turn, leads to the preferred proper placement of the injection device 7 on the patient when the injection device 7 is removed from the base 402. In the illustrated embodiment, the gripping areas or regions 418 and 420 are spaced apart, and preferably opposed, to encourage user holding of the injection device 7 between the thumb and one or more of the fingers of the user's hand (better seen in FIGS. 53B and 53C). As seen in FIG. 47, the periphery of the injection device 7 may also have opposed flattened portions or flats 500 that are located in registration with the preferred gripping areas 418 and 420 of the ring 408 and the preferred gripping areas 403 of the base 402, when the injection device 7 is mounted on the base 402 to further encourage the desired user gripping.

More specifically, in the illustrated structure (which is not exclusive of the structure that may be used), the locator ring 408 defines the preferred holding or gripping areas or regions by the use of opposed portions 418 and 420 of the locator ring 408 that are substantially flush with the support surface 404 when the locator ring or ring structure 408 is mounted thereon. The portions of the locator ring 408 between the holding regions 418 and 420 are configured to form interfering regions (zones or areas) 422 and 424 that tend to block or impede gripping of the transfer device 400 in those regions. More specifically, as shown, the interfering regions 422 and 424 of the locator ring 408 are relatively raised, or elevated from the support surface 404 so as to be located at or above the height of the peripheral edge of the injection device 7 to prevent or as least impede access to the peripheral edge of the injection device 7 in those regions and encourage the patient/user to grip the injection device, instead, in the preferential holding regions or gripping areas 418 and 420.

Figure 49A:
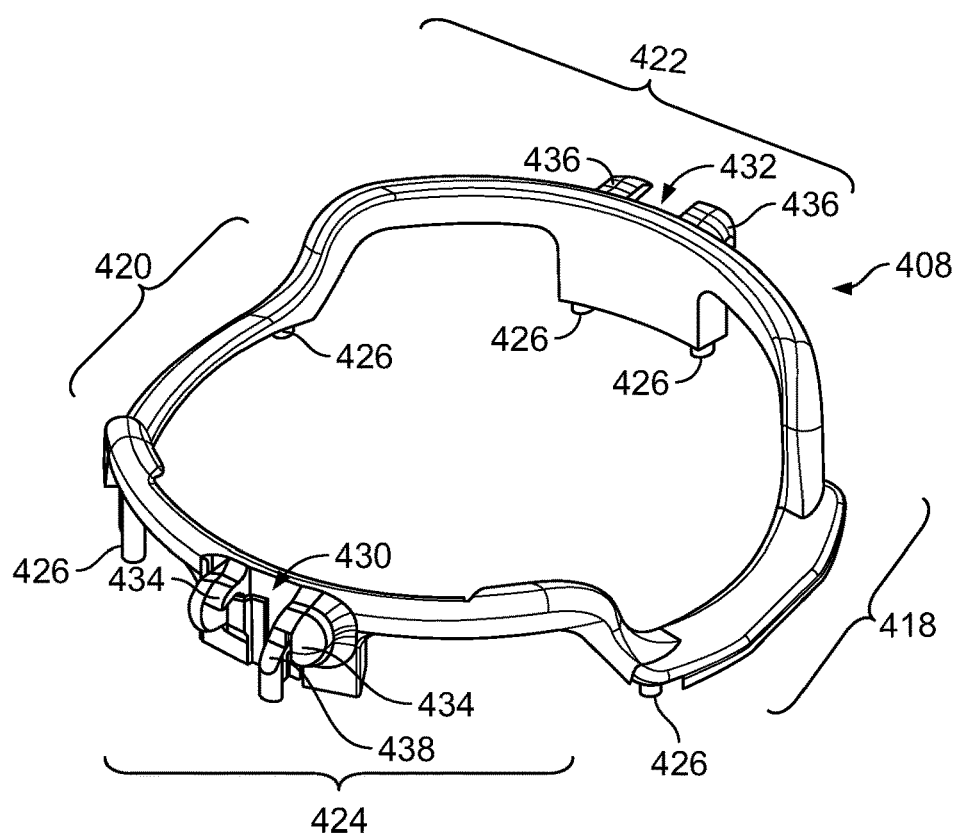
FIGS. 49A and 49B are perspective views of a locator ring that attaches to the transfer device base and within which the injection device nests when the system is assembled.
Figure 49B:
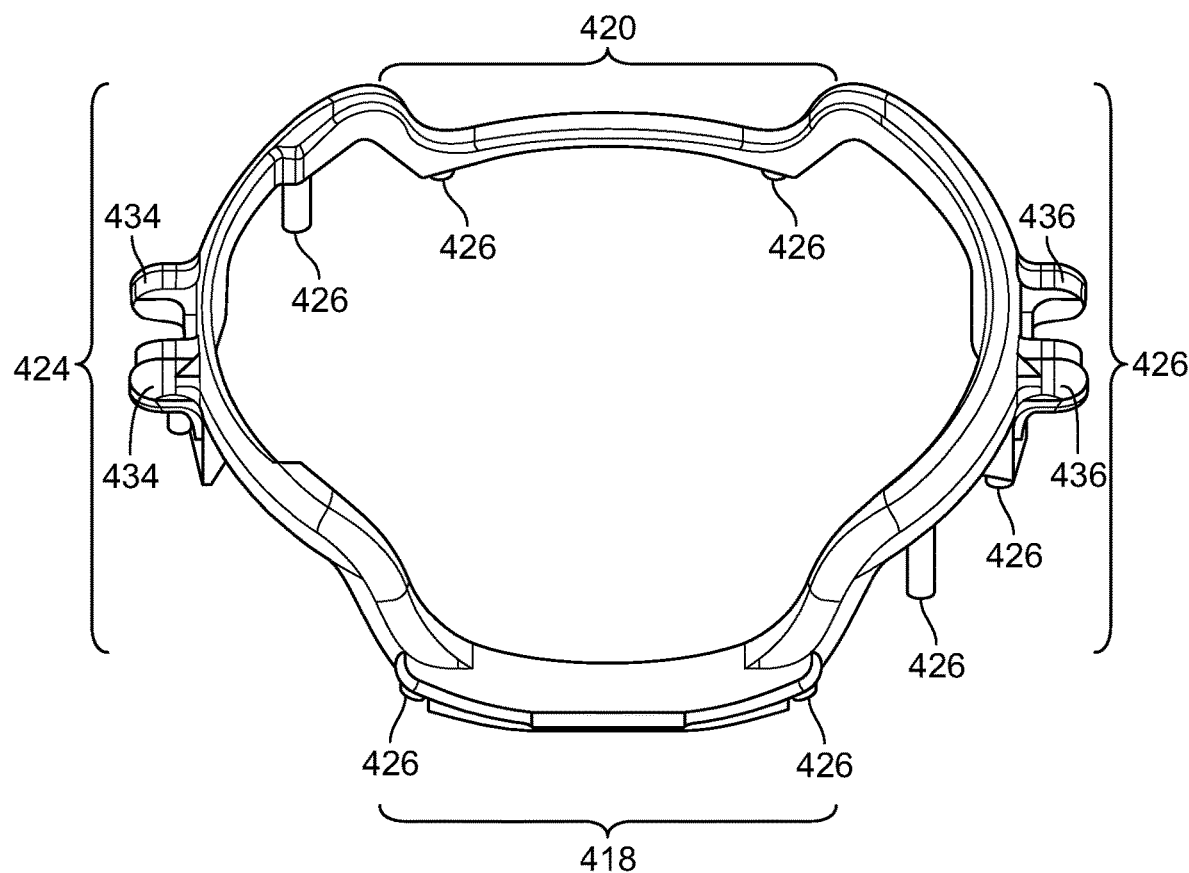

Referring to FIGS. 49a and 49b, where the locator ring 408 may be better viewed, the illustrated (non-limiting) example of a suitable locator ring 408 extends fully 360 degrees and is comprised of opposed gripping areas or holding regions 418 and 420 and opposed interfering regions 422 and 424. Alternatively, for example, raised locator ring segments (e.g., segments that only extend for a limited arc) could potentially be used in the interfering regions and no ring portions would be provided in the gripping areas. Other structures could also be provided that help define preferred gripping areas and interfering areas. Of course, these other structures may not have all the benefits of a locator ring 408 that extends a full 360 degrees to fully encircle the injection device 7.

The illustrated locator ring or ring structure 408 is molded of suitable plastic material that may be bonded or otherwise attached to the base 402, and is of a size or diameter slightly larger than the injection device 7 to allow an injection device 7 to be positioned in a nesting type relationship within the locator ring 408 and resting on the generally flat support surface 404 of base 402. For attachment to the base 402, the locator ring 408 includes connection pins 426 that extend downwardly at predetermined, non-symmetrical locations that coincide with receiving holes or openings 428 (see FIG. 48) located around the periphery of the base 402. This allows the locator ring 408 to be mounted in only a single specific location on the base 402, where the connection pins 426 are in registration with the intended receiving openings 428 into which they are inserted when the locator ring 408 is properly positioned on the base 402. The ring connection pins 426 may extend through the receiving holes 428, with the ends flattened or heat swaged to hold the locator ring 408 on the base 402. Other bonding or attachment configurations may also be used.

In addition to the ergonomic benefits of the locator ring 408, the illustrated ring embodiment also helps protect the injection device 7 during shipping and handling as may be reflected, for example, in drop testing. The locator ring 408 helps protect against impact and also helps prevent undue lateral forces from being applied (upon impact) by the injection device 7 to the upstanding fluid transfer port 416 that extends from the valve 410 through the base 402 and into the injection device 7.

It may be noted that the preferential gripping area or holding region 418 of the locator ring 408 has a generally flattened configuration. As more fully explained below, this region cooperates with a particular feature on the base 402 to form an area that is conducive to placement of the user's thumb when gripping the injection device 7. By providing a predictable gripping position for the user's thumb, proper user placement of the injection device 7 on their abdomen of the user can be more predictably assured. This will be more fully explained with reference to FIGS. 53A-53O.

Figure 50:
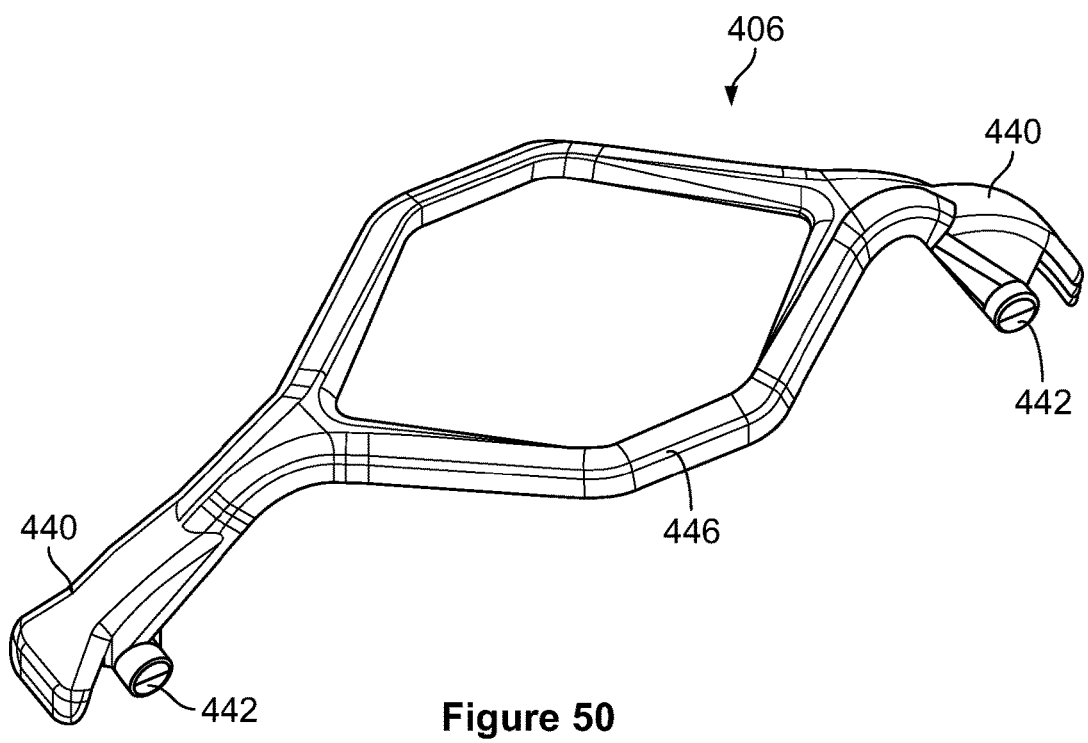
FIG. 50 is a perspective view of a retainer or harness that holds the injection device against the transfer device base.

As with the prior embodiment, the injection device 7 is secured on the base 402 by retainer or harness 406, seen in FIG. 50. The harness 406 holds the injection device on the base 402 during shipping, storage and during many of the preparation steps before an injection. In addition, the harness may have other benefits. First, the harness 406 serves to prevent inadvertent removal of the injection device 7 from the base 402. Also, as can be seen more clearly in FIG. 53B, the harness 406 is located so as to extend over and protect the injection device safety tab 504 (which prevents the actuator button 77 of the injection device from being depressed). In this way, the harness 406 helps prevent mistaken or inadvertent premature removal of the safety tab 504 by the user.

For securing the harness 406, the locator ring 408 has harness mounts 430 and 432 located on opposite sides of the locator ring 408 within the interfering regions 422 and 424. Each harness mount includes a pair of spaced harness pin receivers 434 and 436 and an inclined harness ramp latch 438 therebetween.

In FIG. 50, the illustrated harness 406 is a single elongated molded plastic member that extends from one side of the locator ring 408 to the other side, across the top of the injection device 7 to hold the injection device 7 against the support surface 404. A harness connector 440 is located at each end of the harness 406 for securing the harness 406 to the harness mounts 430 and 432 on the ring 408. Each harness connector 440 has a pair of harness mounting pins 442 for receipt in the harness pin receivers 434 and 436 located on the locator ring 408. To help retain the injection device 7 against lateral shifting on the base 402, the harness 406 may also include an injection device interface structure 446 between the ends of the harness 406. As illustrated, the interface structure 446 is configured as a loop (shown as being hexagonal, but any suitable surrounding configuration is also suitable) that extends around the actuator button 77 of the injection device 7.

Figure 48:
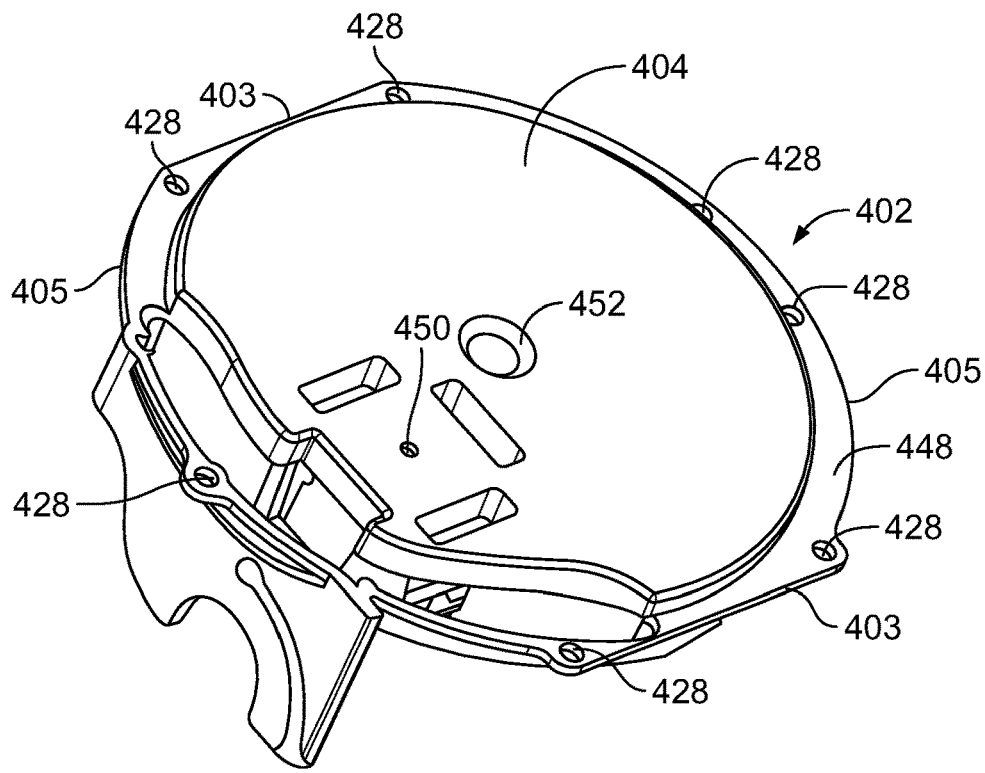
FIG. 48 is a perspective view of the transfer device base against which the injection device rests when the system is assembled.

The base 402 may be seen in perspective view in FIG. 48. The base generally has a peripheral edge surface or flange 448 that extends around the raised planar support surface 404. The receiving openings 428 for the ring connection pins 426 are located, in this embodiment, in the peripheral flange 448. When the base 402 and the locator ring 408 are assembled together, the recessed edge flange 448 cooperates with the locator ring 408 to define the preferential gripping areas 418 and 420. As explained earlier, one or both of the preferential gripping or holding regions 418 and 420 of the locator ring 408 may be of a thickness, such as flattened, so that when resting on the edge flange 448 they are generally flush with the raised support surface 404 upon which the injection device 7 rests. This permits ease of gripping by the user in those areas. In contrast, the interfering areas or regions 422 and 424 of the locator ring 408 extend around the support surface 404 at a height elevated from the support surface 404. In the interfering areas, the locator ring 408 extends generally along the peripheral edge of the injection device 7 as it rests on the support surface 404. This position of the locator ring 408 in the interfering areas 422 and 424 interferes with user gripping of the peripheral edges of the injection device 7 in those interfering areas.

As with the prior embodiment, the support surface 404, upon which the injection device 7 rests, has a fluid transfer port 450, through which fluid/drug is introduced into the injection device 7, and a larger central aperture 452 for accommodating a skin-compressing protrusion (see element 109 in FIGS. 10-12) that is located on the underside of the injection device 7.

Figure 51A:
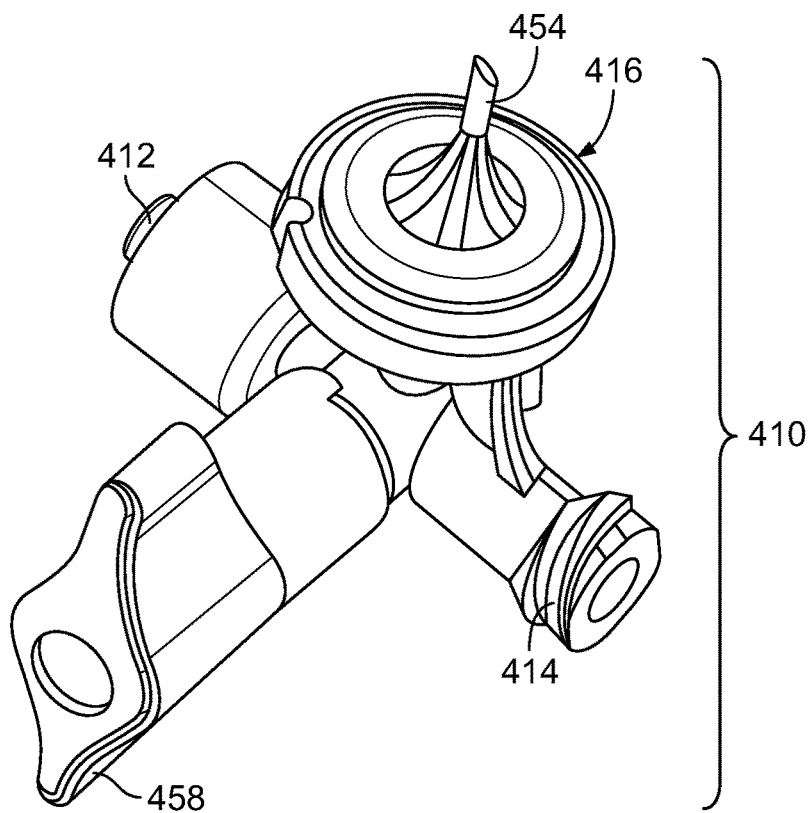
FIG. 51A is a perspective view of a valve subassembly for controlling the flow of fluid among a syringe, a vial and the injection device.
Figure 51B:
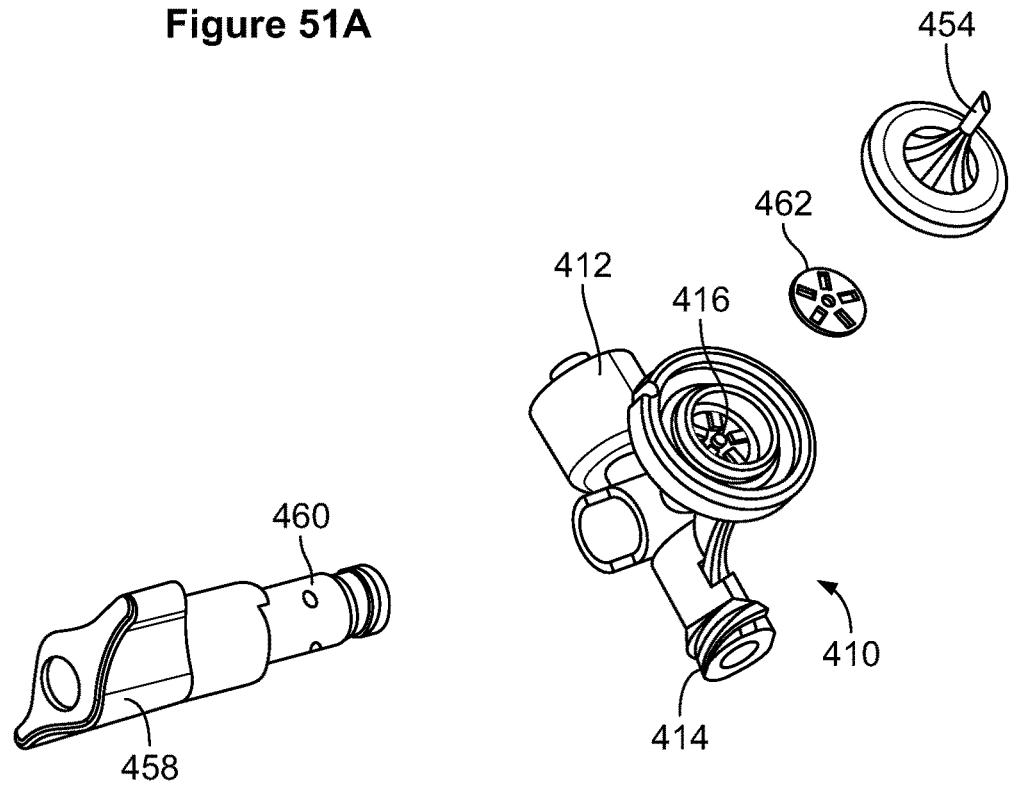

FIGS. 51a and 51b illustrate one embodiment of valve 410 may be secured in any suitable manner to the underside of the base 402. The illustrated valve 410 is a 3-way stopcock assembly that controls flow, as explained earlier, among the vial 240, syringe 242 and injection device 7. Referring to FIG. 51*a*, the valve or stopcock assembly 410 includes the fluid transfer port 416 including an upstanding fluid transfer port tube 454 that extends through fluid transfer port 450 in the support surface 404 of the base 402 for injecting fluid/drug into the injection device 7, the standard syringe female luer lock connection port 414 for connecting to a syringe, such as syringe 242, the male luer lock vial adapter connection port 412 for attaching a vial spike adapter 456 (see FIG. 52) and a valve handle 458 for rotating a valve stem 460 to selectively place the syringe port 414 into communication with the vial adapter connection port 412 or the fluid transfer port 416. As better seen in exploded FIG. 51*b*, a particulate filter 462, such as a nylon membrane or mesh filter, may also be provided in the valve 410 for removing any residual particulate from the fluid or drug as it passes into the fluid transfer port 416 and before it is injected into the injection device 7.

The relative positioning of the valve handle 458 and ports 412, 414 and 416 of the transfer device 400 is configured to provide ease of user grasping and manipulation of the entire assembly. For example, note that the vial adapter connection port 412 and the syringe port 414 extend in opposite directions, with the valve handle 458 being located between them and extending at a right angle relative to the ports 412 and 414. This arrangement allows for user grasping of the transfer device assembly 400 in a manner that provides for ease of operation and manipulation of the valve 410 in a natural and intuitive manner.

Figure 52:
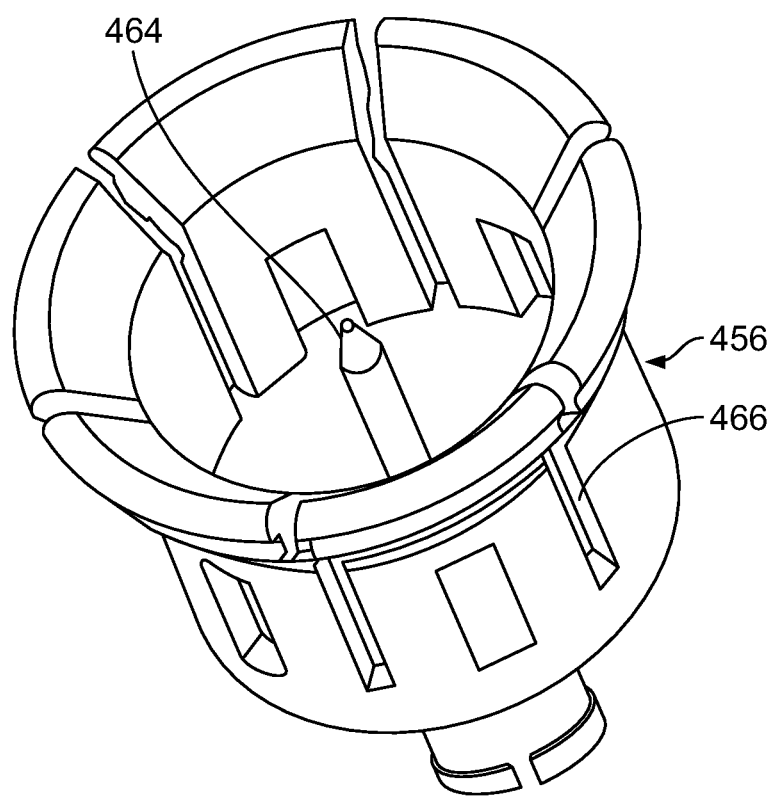
FIG. 52 is a perspective view of vial adaptor for receiving a vial of medicament.

FIG. 52 shows the standard vial spike adapter 456 configured for mounting on the luer-type vial adapter connector port 412. The vial adapter 456 includes an internal spike 464 for puncturing a vial septum, and an outer shield 466 to protect against inadvertent touching of the spike 464 and to help guide a vial into the vial adapter 456.

Figure 53O:
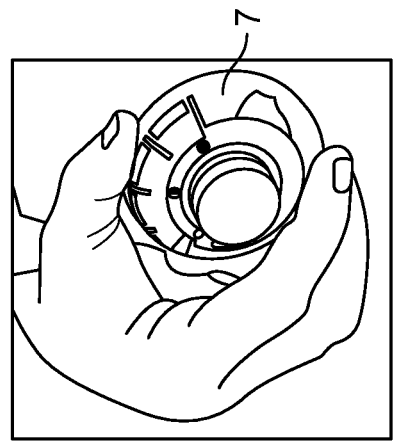
Figure 53N:
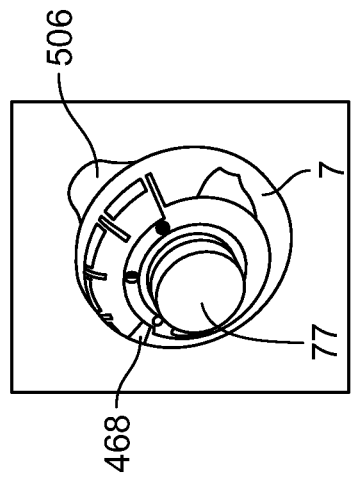

FIGS. 53A-53O illustrate preparation and use of the transfer device 400 and an associated injection device 7, consistent with the system 401 shown in FIG. 47. FIGS. 53A-53J show the PREPARATION steps leading to attachment of the injection device 7. From left to right and top to bottom, the vial spike adapter 456 is provided as a separate part in its own packaging. The user opens the package and inserts the desired vial 240 into the vial adapter 456, using aseptic technique to avoid contamination. The vial adapter 456, with inserted vial 240, is then connected to the vial adapter connection port 412 of the valve 410 (which is mounted to the underside of the base 402. A syringe 242 is then connected to the syringe connection port 414 of the valve 410, also using aseptic technique—which should be understood to be employed throughout the preparation without the need for further mention. The valve handle 458 is set to allow the syringe 242 to withdraw fluid, such as a drug or other medicament, from the vial 240. The valve handle 458 is then rotated to open the flow path between the syringe 242 and the fluid transfer port 416, which includes upstanding tube 454 that extends through the base 402 and into the injection device filling port 81. The syringe plunger is depressed to force fluid from the syringe 242 into the injection device 7 until the desired dose is introduced, which may require multiple vials 240.

Continuing through the PREPARATION illustrations of FIGS. 53A-53J, after preparation of the injection site on the patient's abdomen, the harness 406 is released and the injection device 7 is grasped in the preferential gripping or holding areas or regions (as explained above) and removed from the base 402. Removal may simultaneously and without further user action, remove a protective film that covers a layer of adhesive on the underside of the injection device 7. Alternatively, the protective film may be manually removed. The injection device 7 is then attached to the patient's skin, with adhesive on the underside of the injection device 7 retaining the injection device 7 on the patient temporarily during the injection. As seen in the final preparation illustrations, the injection device 7 preferably includes a movable internal indicator or gauge 468 and graduated markings 470 on the injector housing, which indicate the fill condition of the injection device 7 and show to the user the status or progress of the fill and/or injection. These features are more fully described in U.S. Provisional Patent Application No. 62/449,247 filed Jan. 23, 2017, which is hereby incorporated by reference in its entirety. The preferential gripping areas 418 and 420 discussed at length above are located to encourage the user to naturally or instinctively place the injector device 7 on the skin of the abdomen with the indicator and markings being on the upper side of the injection device 7 and easily visible to the user when the user looks downwardly toward his or her abdomen.

Figure 54:
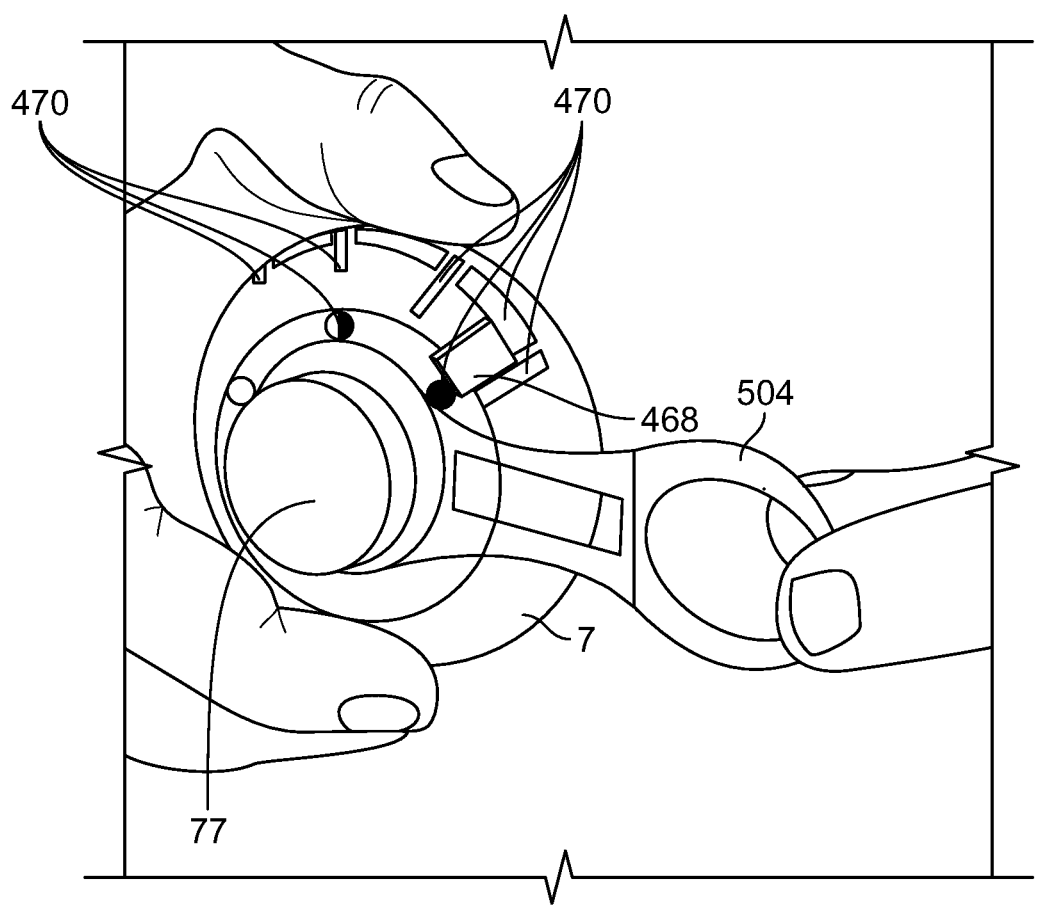
FIG. 54 is a perspective view of the injection device as it preferably is located on a patient, illustrating the ergonomic features that encourage user positioning that allows viewing of the injection status indicator.

Turning now to the "INFUSE" illustrations in FIGS. 53K-53O and also referring to FIG. 54, the preferential holding areas 418 and 420 and resultant natural positioning of the injection device 7 on the abdomen also serve to point the release safety tab 504 in the direction of the user's free hand that is not holding the injection device 7. This ergonomic benefit allows the user to continue to grasp and secure the injection device 7 while pulling and removing the safety tab 504 to prepare the device for injection and after removal of the safety tab 504, as shown, to press the injection button 77 with the free hand—at which point the injection needle is advanced into the patient's skin and flow of medicament is started. The preferential placement of the injection device 7 on the abdomen allows the movable indicator and graduated markings to be readily visible to the patient for monitoring injection progress.

When the injection is completed, as shown in the "DONE" illustrations, the injection device 7 is gripped, including a tab 506 that is associated with the adhesive attachment member and extends radially outwardly for ease of gripping with the injection device 7. Removal of the injection device 7 from the skin simultaneously lifts the tab 506 and pulls the adhesive member from the skin.

Further Alternative Embodiments

Figure 55:
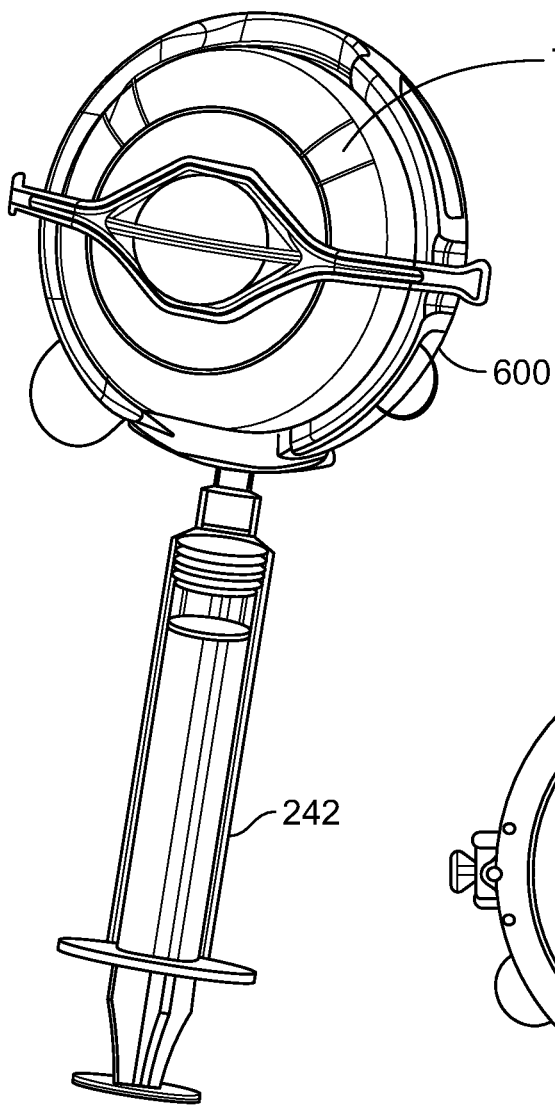
FIG. 55 is a perspective view of a hand-held transfer device, injection device mounted thereon and syringe, in which the injection device does not have a manual valve for controlling fluid flow.
Figure 56:
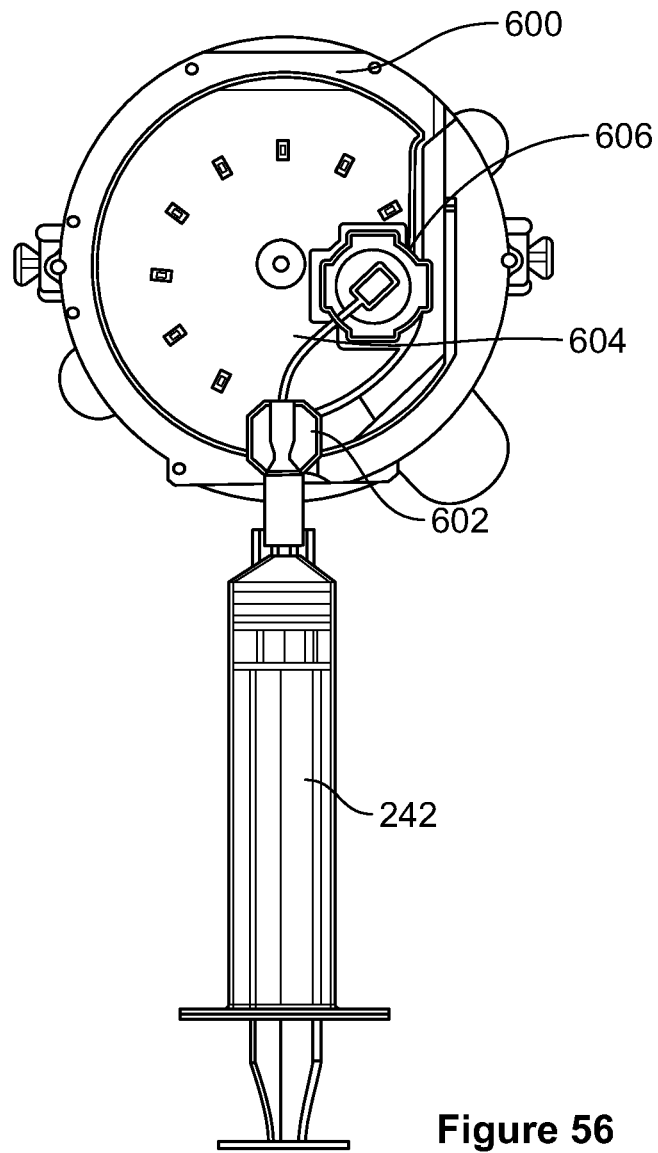
FIG. 56 is bottom view of the hand-held transfer device shown in FIG. 55.
Figure 57:
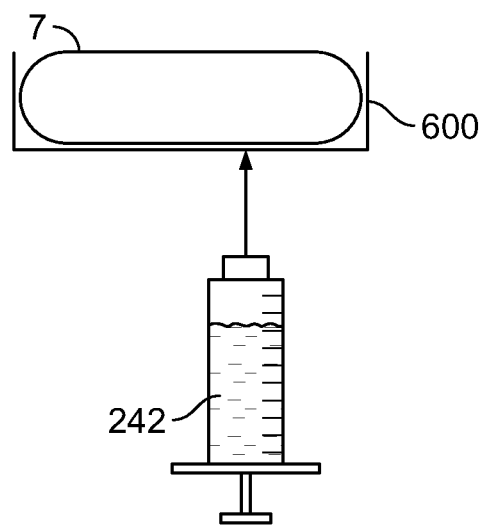
FIGS. 57-60 are diagrammatic illustrations of a few examples of potential uses of the hand-held transfer device of FIGS. 55 and 56.

Although the illustrated embodiments have been shown as configured for transfer of medical fluid from a vial into the injection device with a manual flow control valve, those are not the exclusive applications of the hand-held transfer device of the present application. FIGS. 55 and 56 show a hand-held transfer device without a manual fluid flow control valve.

FIG. 55 is a perspective view of an assembled system including a hand-held transfer device 600 (without a manual flow control valve), with an injection device or injector 7 mounted thereon and a standard syringe 242 secured to the transfer device 600. The transfer device 600 is essentially the same as that described earlier, except that it does not have a manual flow control valve. As best see in FIG. 56, the hand-held transfer device includes a syringe port 602 that is directly connected by flow tubing 604 to a fluid transfer port assembly 606 that extends from the support surface (not shown) of the transfer device as previously described for introduction of medical fluid into the injection device 7. No flow control valve or vial port of vial adapter is needed.

FIGS. 57-60 show diagrammatic examples of how the hand-held transfer device 600 may be used. For example, in FIG. 57 the medical fluid could be provided in a pre-filled syringe 242, and injected directly into transfer device 600 for introduction the injection device 7. In such a configuration, no vial port, vial adapter or manual flow control valve of any type would be required. The illustrated injection device 7 has a built-in one-way valve that prevents backflow of medical fluid from the reservoir located in the injection device 7, so in this configuration, no fluid flow control valve is needed.

Figure 58:
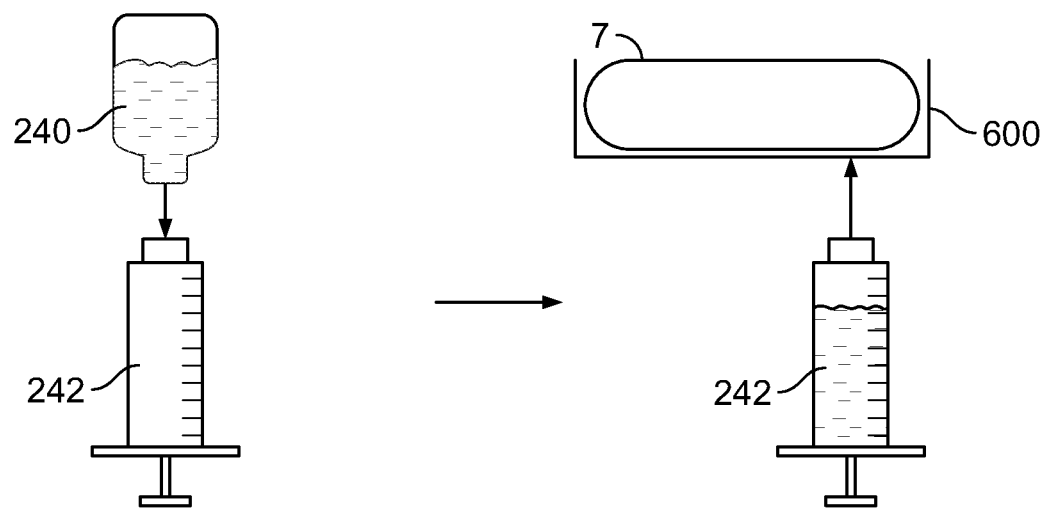

Alternatively, in FIG. 58 the syringe 242 may not be pre-filled by the drug manufacturer, but medical fluid may be withdrawn from a vial 240 directly into a syringe 242 via a standard vial adapter, and then the filled syringe 242 could be detached from the vial adapter and attached to the transfer device 600 to inject the medical fluid directly through the transfer device 600 into the injection device 7 mounted thereon—and no manual valve, vial port or adapter would be needed on the transfer device 600.

Figure 59:
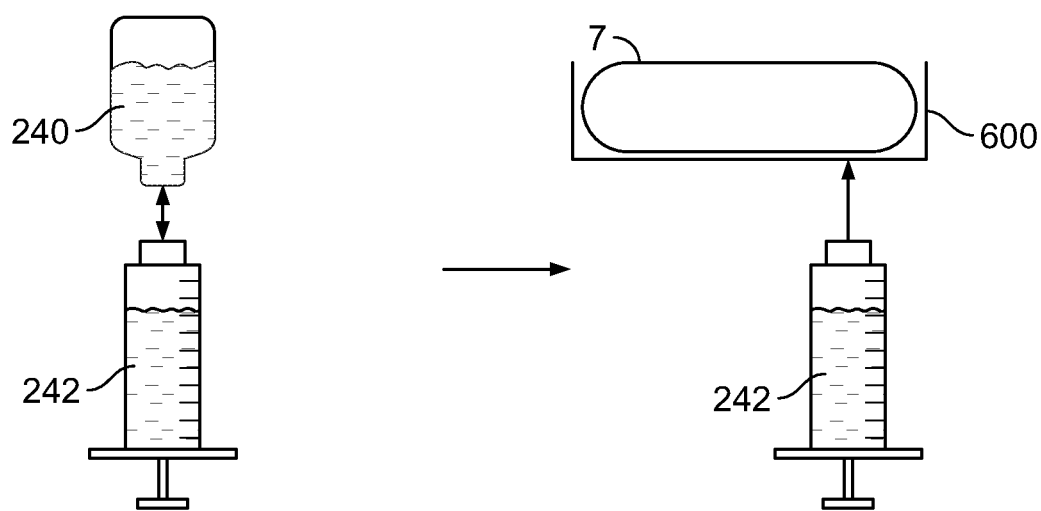

A further alternative configuration/method, shown in FIG. 59, does not require a transfer device with a manual valve, could employ a syringe 242 prefilled with diluent and a vial 240 with powdered (e.g., lyophilized) or concentrated liquid medical fluid/drug. The syringe 242 would be attached to the vial 240 using a standard vial adapter and the drug reconstituted or diluted with diluent from the vial 240, and then drawn into the syringe 242. The syringe 242 would be detached from the vial adapter, attached to the transfer device 600 and the reconstituted medical fluid injected directly into the injection device 7. As with the alternative described earlier, no valve, vial port or adapter would be needed on the transfer device 600 for this application.

Figure 60:
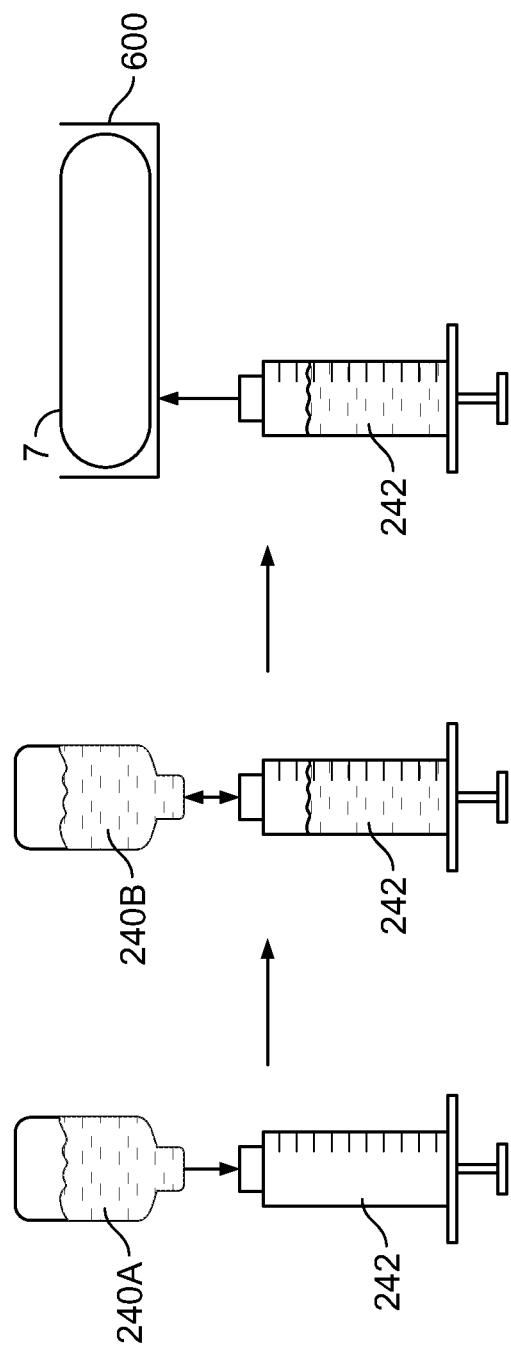

A further variation of the preceding example that would not require a valve on the transfer device 600, as shown in FIG. 60, would use two vials—a vial 240A with diluent fluid, a vial 240B with powdered or concentrated liquid drug, an empty syringe 242 and a vial adapter for each vial. The syringe 242 could be used to draw diluent from the diluent vial 240A, via a diluent vial adapter, and then, after disconnection from the diluent vial adapter, be attached to the drug vial 240B, via the drug vial adapter and thereby reconstitute the powdered drug or dilute the concentrated drug. The diluted or reconstituted drug/medical fluid would be drawn into the syringe 242 and the syringe 242 disconnected from the drug vial adapter and attached directly to the hand-held transfer device 600, for injecting the prepared drug/medical fluid directly into the injection device 7.

These are but a few of the possible variations on the configuration and/or use of the hand-held transfer device described herein. For example, a hand-held transfer device could include an attached vial adapter and have no valve.

Although the present subject matter is described herein with reference to specific structures, methods and examples, this is for purposes of illustration only, and it is understood that the present subject matter is applicable to a large range of devices and systems that may differ in particular configuration and appearance while still employing this subject matter.

The invention claimed is:

1. A disposable transfer device comprising: a base having a support surface configured to receive an on-body injection device; a fluid transfer port extending upwardly from the support surface and configured to transfer liquid into an injection device when the injection device is received on the support surface; a vial adapter configured to receive a vial; a syringe adapter configured to receive a syringe; a fluid flow path configured to selectively be placed in communication between the vial adapter and syringe adapter and to selectively be placed in communication between the syringe adapter and the fluid transfer port; and a valve in communication with the fluid flow path and configured to selectively place the vial adapter in communication with the syringe adapter or place the syringe adapter in communication with the fluid transfer port.

2. The disposable transfer device of claim 1 further comprising a lower surface opposed to the support surface, and wherein the valve and fluid flow path are connected to the lower surface.

3. The disposable transfer device of claim 1 wherein the valve further comprises a manually adjustable valve.

4. The disposable transfer device of claim 1 further comprising a second vial adapter configured to receive a second vial and being in communication with the fluid flow path.

5. The disposable transfer device of claim 1 further comprising a releasable harness configured to couple an injection device to the transfer device.

6. The disposable transfer device of claim 5 wherein the harness is configured to hold an injection device against the support surface of the transfer device and to resist lateral shifting of the injection device on the support surface.

7. The disposable transfer device of claim 1 in combination with an injection device releasably held in a coupled position to the disposable transfer device.

8. The disposable transfer device in combination with the injection device of claim 7 wherein the injection device further comprises an internal resilient expandable member and a filling port for introducing liquid into the resilient expandable member and wherein the fluid transfer port of the transfer device extends into the filling port of the injection device when the injection device is coupled to the transfer device.

9. The disposable transfer device of claim 1 further comprising preferential gripping areas for user gripping of an injection device when the injection device is located on the support surface and interfering areas for interfering with user gripping of the injection device in the interfering areas when the injection device is located on the support surface.

10. The disposable transfer device of claim 9 wherein the base further comprises raised arcuate segments defining the interfering areas and spaces between the raised segments defining the preferential gripping areas.

11. The disposable transfer device of claim 9 wherein the preferential gripping areas are defined adjacent the support surface.

12. The disposable transfer device of claim 9 further comprising a locator ring extending around the support surface and defining the preferential gripping areas and the interfering areas.

* * * * *